(12) United States Patent
Wang

(10) Patent No.: US 12,159,331 B2
(45) Date of Patent: *Dec. 3, 2024

(54) SYSTEMS AND METHODS FOR EVALUATING IMAGE QUALITY

(71) Applicant: SHANGHAI UNITED IMAGING HEALTHCARE CO., LTD., Shanghai (CN)

(72) Inventor: Yi Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,737

(22) Filed: Jun. 26, 2023

(65) Prior Publication Data

US 2023/0351649 A1  Nov. 2, 2023

Related U.S. Application Data

(63) Continuation of application No. 17/651,895, filed on Feb. 21, 2022, now Pat. No. 11,688,110, which is a (Continued)

(30) Foreign Application Priority Data

| Jun. 11, 2018 | (CN) | 201810597965.1 |
| Sep. 27, 2018 | (CN) | 201811133609.0 |

(Continued)

(51) Int. Cl.
  *G06T 11/00* (2006.01)
  *A61B 5/00* (2006.01)
  (Continued)

(52) U.S. Cl.
  CPC ............ *G06T 11/008* (2013.01); *A61B 5/489* (2013.01); *A61B 6/032* (2013.01); *A61B 6/503* (2013.01);
  (Continued)

(58) Field of Classification Search
  CPC .. G06T 11/005; G06T 11/008; G06T 11/0014; G06T 7/11; G06T 7/90;
  (Continued)

(56) References Cited

U.S. PATENT DOCUMENTS

| 5,764,813 A | 6/1998 | Murayama et al. |
| 6,522,712 B1 | 2/2003 | Yavuz et al. |

(Continued)

FOREIGN PATENT DOCUMENTS

| CN | 101352352 A | 1/2009 |
| CN | 101727666 A | 6/2010 |

(Continued)

OTHER PUBLICATIONS

Guo, Qi et al., Summarize of Evaluation Methods for Image Segmentation, Proceedings of the 9th Youth Academic Conference of China Instrument and Control Society, 2007, 6 pages.

(Continued)

*Primary Examiner* — Gabriel I Garcia
(74) *Attorney, Agent, or Firm* — METIS IP LLC

(57) ABSTRACT

A method for reconstructing a target cardiac image is provided. The method may include: determining a quality index for each cardiac image of a plurality of cardiac images corresponding to one or more cardiac motion phases; determining a phase of interest base on the plurality of quality indexes; and obtaining the target cardiac image of the phase of interest.

20 Claims, 14 Drawing Sheets

Related U.S. Application Data continuation of application No. 17/326,374, filed on May 21, 2021, now Pat. No. 11,367,228, which is a continuation of application No. 16/437,006, filed on Jun. 11, 2019, now Pat. No. 11,024,062.

(30) Foreign Application Priority Data

| | | |
|---|---|---|
| Sep. 27, 2018 | (CN) | 201811133622.6 |
| Sep. 27, 2018 | (CN) | 201811134373.2 |
| Sep. 27, 2018 | (CN) | 201811134375.1 |

(51) Int. Cl.

| | |
|---|---|
| *A61B 6/03* | (2006.01) |
| *A61B 6/50* | (2024.01) |
| *G06T 5/20* | (2006.01) |
| *G06T 5/50* | (2006.01) |
| *G06T 5/73* | (2024.01) |
| *G06T 7/00* | (2017.01) |
| *G06T 7/11* | (2017.01) |
| *G06T 7/90* | (2017.01) |
| *A61B 6/00* | (2006.01) |

(52) U.S. Cl.
CPC ............... *A61B 6/504* (2013.01); *G06T 5/20* (2013.01); *G06T 5/50* (2013.01); *G06T 5/73* (2024.01); *G06T 7/0014* (2013.01); *G06T 7/11* (2017.01); *G06T 7/90* (2017.01); *G06T 11/005* (2013.01); *A61B 6/481* (2013.01); *A61B 6/541* (2013.01); *G06T 2207/10072* (2013.01); *G06T 2207/20201* (2013.01); *G06T 2207/30048* (2013.01); *G06T 2207/30101* (2013.01); *G06T 2207/30168* (2013.01); *G06T 2211/404* (2013.01); *G06T 2211/412* (2013.01)

(58) Field of Classification Search
CPC ........... G06T 7/0014; G06T 5/73; G06T 5/20; G06T 5/50; G06T 2207/10072; G06T 2207/20201; G06T 2207/30048; G06T 2207/30101; G06T 2207/30168; G06T 2211/404; G06T 2211/412; A61B 5/489; A61B 6/032; A61B 6/481; A61B 6/503; A61B 6/504; A61B 6/541
USPC .......................................................... 382/131
See application file for complete search history.

(56) References Cited

U.S. PATENT DOCUMENTS

| | | | |
|---|---|---|---|
| 6,539,074 | B1 | 3/2003 | Yavuz et al. |
| 10,555,702 | B1 | 2/2020 | Couderc et al. |
| 11,024,062 | B2 | 6/2021 | Wang |
| 2003/0002616 | A1 | 1/2003 | Cesmeli |
| 2007/0073114 | A1 | 3/2007 | Gundel |
| 2007/0248253 | A1 | 10/2007 | Manzke et al. |
| 2008/0075343 | A1 | 3/2008 | John et al. |
| 2009/0003513 | A1 | 1/2009 | Grass et al. |
| 2009/0232379 | A1 | 9/2009 | Kohler et al. |
| 2010/0074485 | A1 | 3/2010 | Movassaghi et al. |
| 2012/0229829 | A1 | 9/2012 | Hara |
| 2012/0275673 | A1 | 11/2012 | Star-Lack et al. |
| 2014/0219524 | A1 | 8/2014 | Takeguchi et al. |
| 2014/0227682 | A1 | 8/2014 | Seth et al. |
| 2015/0022523 | A1 | 1/2015 | Murray et al. |
| 2015/0348277 | A1 | 12/2015 | Frinking |
| 2016/0035112 | A1 | 2/2016 | Lou et al. |
| 2016/0171716 | A1 | 6/2016 | Schafer et al. |
| 2016/0321821 | A1* | 11/2016 | Brown ............. G06T 3/20 |
| 2016/0354158 | A1* | 12/2016 | Razavi ............. A61B 5/318 |
| 2017/0030990 | A1 | 2/2017 | Janich et al. |
| 2017/0069105 | A1 | 3/2017 | Kano et al. |
| 2017/0083742 | A1 | 3/2017 | Lamare et al. |
| 2017/0148157 | A1 | 5/2017 | Ninomiya |
| 2017/0178285 | A1 | 6/2017 | Jiang et al. |
| 2017/0196527 | A1 | 7/2017 | Kokubun |
| 2017/0249740 | A1 | 8/2017 | Brehm et al. |
| 2017/0301066 | A1 | 10/2017 | Wang et al. |
| 2017/0323587 | A1* | 11/2017 | Yagi ............. G09B 23/30 |
| 2018/0315191 | A1 | 11/2018 | Meng et al. |
| 2018/0353098 | A1 | 12/2018 | Ye et al. |
| 2019/0378309 | A1 | 12/2019 | Wang |

FOREIGN PATENT DOCUMENTS

| | | |
|---|---|---|
| CN | 102609939 A | 7/2012 |
| CN | 102622775 A | 8/2012 |
| CN | 102663747 A | 9/2012 |
| CN | 102800111 A | 11/2012 |
| CN | 102982542 A | 3/2013 |
| CN | 103337071 A | 10/2013 |
| CN | 103356241 A | 10/2013 |
| CN | 103390274 A | 11/2013 |
| CN | 104240180 A | 12/2014 |
| CN | 104331914 A | 2/2015 |
| CN | 104545973 A | 4/2015 |
| CN | 104657984 A | 5/2015 |
| CN | 104794714 A | 7/2015 |
| CN | 104867147 A | 8/2015 |
| CN | 105354835 A | 2/2016 |
| CN | 106296764 A | 1/2017 |
| CN | 106780651 A | 5/2017 |
| CN | 107049475 A | 8/2017 |
| CN | 107468267 A | 12/2017 |
| CN | 107483920 A | 12/2017 |
| CN | 108182720 A | 6/2018 |
| CN | 108898582 A | 11/2018 |
| CN | 109345606 A | 2/2019 |
| CN | 109389653 A | 2/2019 |
| DE | 102006037601 A1 | 2/2008 |
| EP | 1008860 A2 | 6/2000 |
| WO | 03030101 A2 | 4/2003 |
| WO | 2009070300 A1 | 6/2009 |
| WO | 2013177779 A1 | 12/2013 |
| WO | 2015164761 A1 | 10/2015 |

OTHER PUBLICATIONS

Pratomo Adhi Nugroho et al., 3D Heart Image Reconstruction and Visualization with Marching Cubes Algorithm, 2016 International Conference on Knowledge Creation and Intelligent Computing (KCIC), 2016, 7 pages.

Jiang, Jun et al., Three Dimensional Reconstruction of Heart Based on Chinese Digitized Visible Human, Journal of Tissue Engineering and Reconstructive Surgery, 10(1): 8-10, 2014.

Thomas Kohler et al., Automatic No-Reference Quality Assessment for Retinal Fundus Images Using Vessel Segmentation, Proceedings of the 26th IEEE International Symposium on Computer-Based Medical Systems IEEE (CBMS), 2013, 6 pages.

* cited by examiner

SYSTEMS AND METHODS FOR EVALUATING IMAGE QUALITY

CROSS-REFERENCE TO RELATED APPLICATIONS

This application is a continuation of U.S. application Ser. No. 17/651,895, filed on Feb. 21, 2022, which is a continuation of U.S. application Ser. No. 17/326,374 (issued as U.S. Pat. No. 11,367,228), filed on May 21, 2021, which is a continuation of U.S. application Ser. No. 16/437,006 (issued as U.S. Pat. No. 11,024,062), filed on Jun. 11, 2019, which claims priority to Chinese Patent Application No. 201811134373.2, filed on Sep. 27, 2018, Chinese Patent Application No. 201811134375.1, filed on Sep. 27, 2018, Chinese Patent Application No. 201811133622.6, filed on Sep. 27, 2018, Chinese Patent Application No. 201811133609.0, filed on Sep. 27, 2018, and Chinese Patent Application No. 201810597965.1, filed on Jun. 11, 2018, the contents of each of which are hereby incorporated by reference in its entirety.

TECHNICAL FIELD

The present disclosure relates to image technology, and more specifically relates to systems and methods for evaluating image quality.

BACKGROUND

Angiography is an auxiliary examination technique that is widely used in the diagnosis and treatment of various clinical diseases. Angiography can help doctors to diagnose diseases in time, control the deterioration of the diseases, and effectively improve the survival rate of patients. Therefore, the image quality of angiography images is crucial for the diagnosis of diseases.

In clinical application, a feasible way for the image quality evaluation of angiography images relies on a visual assessment of reconstructed images by a user (e.g., a doctor, an imaging technician, a healthcare provider) which may be subjective. In coronary angiography, the heart beats can produce motion artifacts, and the doctors need to choose appropriate reconstruction phase(s) to obtain qualified cardiac image(s) that can be used for diagnosis. Accordingly, a series of images may need to be generated by computer(s), and evaluated through a user interaction interface. After the visual assessment by the user, a specific reconstruction phase may be selected for cardiac image reconstruction. However, the visual assessment of image quality in the image processing may make the reconstruction process complicated, increase the burden on the user for image quality assessment, cause inconsistent image processing due to, e.g., variations between assessments by different users, slow down the image processing, make it difficult or impossible to automate the image processing, and/or induce repetitious image reconstruction and assessment.

Therefore, it is desirable to provide systems and methods for evaluating image quality automatically or semi-automatically, reconstructing cardiac images that have relatively high image qualities and are affected by cardiac motion to a minimum extent, efficiently, cost-effectively, and without waste of time and/or resources.

SUMMARY

In one aspect of the present disclosure, a method for evaluating image quality is provided. The method may include one or more of the following operations: obtaining an image, the image including a plurality of elements, each element of the plurality of elements being a pixel or voxel, each element having a gray level; determining, based on a maximum gray level of the plurality of elements, one or more thresholds for segmenting the image; determining one or more sub-images of a region of interest by segmenting, based on the one or more thresholds, the image; and determining, based on the one or more sub-images of the region of interest, a quality index for the image.

In another aspect of the present disclosure, a method for reconstructing a target cardiac image is provided. The target cardiac image may include a plurality of elements, and each element of the plurality of elements may be a pixel or voxel. The method may include one or more of the following operations: obtaining projection data generated by an imaging device, the projection data including a plurality of sub-sets of projection data, each sub-set of projection data corresponding to a cardiac motion phase; obtaining a plurality of cardiac images corresponding to one or more cardiac motion phases based on the plurality of sub-sets of projection data corresponding to the one or more cardiac motion phases; determining a quality index for each cardiac image of the plurality of cardiac images; determining a phase of interest base on the plurality of quality indexes; and obtaining the target cardiac image of the phase of interest.

In another aspect of the present disclosure, a system for evaluating image quality is provided. The system may include at least one storage device storing a set of instructions; and at least one processor in communication with the storage device, wherein when executing the set of instructions, the at least one processor may be configured to cause the system to perform one or more of the following operations: obtaining an image, the image including a plurality of elements, each element of the plurality of elements being a pixel or voxel, each element having a gray level; determining, based on a maximum gray level of the plurality of elements, one or more thresholds for segmenting the image; determining one or more sub-images of a region of interest by segmenting, based on the one or more thresholds, the image; and determining, based on the one or more sub-images of the region of interest, a quality index for the image.

In another aspect of the present disclosure, a system for reconstructing a target cardiac image is provided. The system may include at least one storage device storing a set of instructions; and at least one processor in communication with the storage device, wherein when executing the set of instructions, the at least one processor may be configured to cause the system to perform one or more of the following operations: obtaining projection data generated by an imaging device, the projection data including a plurality of sub-sets of projection data, each sub-set of projection data corresponding to a cardiac motion phase; obtaining a plurality of cardiac images corresponding to one or more cardiac motion phases based on the plurality of sub-sets of projection data corresponding to the one or more cardiac motion phases; determining a quality index for each cardiac image of the plurality of cardiac images; determining a phase of interest base on the plurality of quality indexes; and obtaining the target cardiac image of the phase of interest.

In another aspect of the present disclosure, a system is provided. The system may include an obtaining module configured to obtain an image, the image including a plurality of elements, each element of the plurality of elements being a pixel or voxel, each element having a gray level; an ROI image extracting module configured to: determine, based on a maximum gray level of the plurality of elements, one or more thresholds for segmenting the image; and determine one or more sub-images of a region of interest by segmenting, based on the one or more thresholds, the image; and an image quality evaluation module configured to determine, based on the one or more sub-images of the region of interest, a quality index for the image.

In another aspect of the present disclosure, a system is provided. The system may include an image selection module configured to obtain projection data generated by an imaging device, the projection data including a plurality of sub-sets of projection data, each sub-set of projection data corresponding to a cardiac motion phase; and obtain a plurality of cardiac images corresponding to one or more cardiac motion phases based on the plurality of sub-sets of projection data corresponding to the one or more cardiac motion phases; a quality index determination module configured to determine a quality index for each cardiac image of the plurality of cardiac images; and an image reconstruction module configured to determine a phase of interest base on the plurality of quality indexes; and obtain the target cardiac image of the phase of interest.

In another aspect of the present disclosure, a non-transitory computer readable medium storing instructions is provided. The instructions, when executed by at least one processor, may cause the at least one processor to implement a method including: obtaining an image, the image including a plurality of elements, each element of the plurality of elements being a pixel or voxel, each element having a gray level; determining, based on a maximum gray level of the plurality of elements, one or more thresholds for segmenting the image; determining one or more sub-images of a region of interest by segmenting, based on the one or more thresholds, the image; and determining, based on the one or more sub-images of the region of interest, a quality index for the image.

In another aspect of the present disclosure, a non-transitory computer readable medium storing instructions is provided. The instructions, when executed by at least one processor, may cause the at least one processor to implement a method including: obtaining projection data generated by an imaging device, the projection data including a plurality of sub-sets of projection data, each sub-set of projection data corresponding to a cardiac motion phase; obtaining a plurality of cardiac images corresponding to one or more cardiac motion phases based on the plurality of sub-sets of projection data corresponding to the one or more cardiac motion phases; determining a quality index for each cardiac image of the plurality of cardiac images; determining a phase of interest base on the plurality of quality indexes; and obtaining the target cardiac image of the phase of interest.

As illustrated above, the methods, systems, computing devices, and computer readable storage mediums for evaluating image qualities and/or reconstructing cardiac images, may determine a maximum gray level of an image (or each image), and/or designate the maximum gray level multiplied by one or more predetermined multiples as the threshold(s) for segmenting the image; and/or segment the image to be evaluated based on the segmentation thresholds to obtain a vascular image of interest. According to the vascular images of interest, the quality indexes of the corresponding images to be evaluated may be determined, and the image quality of the images to be evaluated may be evaluated according to the quality indexes. The methods can automatically (or semi-automatically) evaluate image qualities of images of corresponding cardiac motion phases, simplify reconstruction processes, reduce the burden on the doctor for image quality evaluation, avoid repeated image quality evaluation, improve the accuracy of the mean phase or phase of interest determined for cardiac image reconstruction, and further improve the quality of the reconstructed cardiac images.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
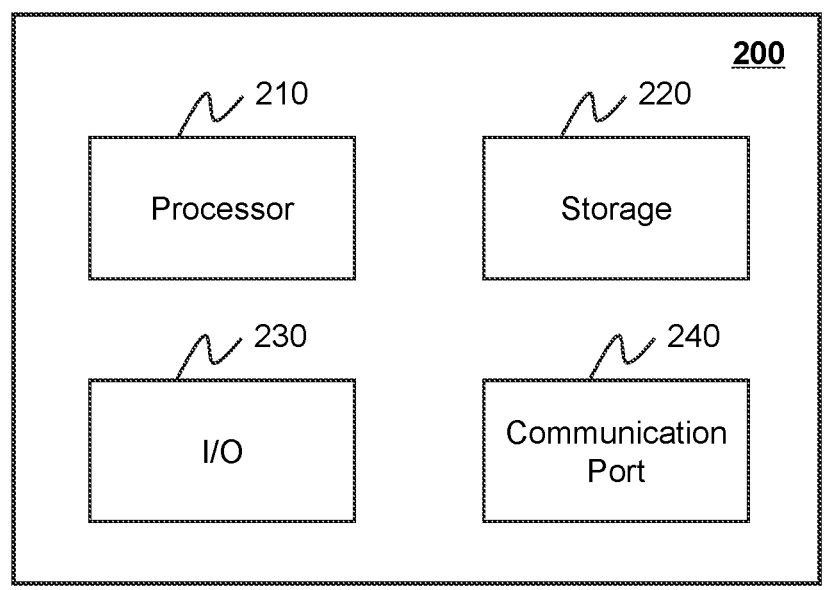
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

For brevity, an image, or a portion thereof (e.g., a region of interest (ROI) in the image) corresponding to an object (e.g., a tissue, an organ, a tumor, etc., of a subject (e.g., a patient, etc.)) may be referred to as an image, or a portion thereof (e.g., an ROI) of or including the object, or the object itself. For instance, an ROI corresponding to the image of a blood vessel may be described as that the ROI includes a blood vessel. As another example, an image of or including a blood vessel may be referred to a vascular image, or simply a blood vessel. For brevity, that a portion of an image corresponding to an object is processed (e.g., extracted, segmented, etc.) may be described as the object is processed. For instance, that a portion of an image corresponding to a blood vessel is extracted from the rest of the image may be described as that the blood vessel is extracted.

One aspect of the present disclosure relates to methods, systems, computing devices, and computer readable storage mediums for evaluating image qualities and/or reconstructing cardiac images, which may obtain an image; determine, based on a maximum gray level of the plurality of elements of the image, one or more thresholds for segmenting the image; determine one or more sub-images of a region of interest by segmenting, based on the one or more thresholds, the image; and/or determine, based on the one or more sub-images of the region of interest, a quality index for the image. The methods can include automatically or semi-automatically evaluating image quality of a plurality of images, determining a mean phase or phase of interest based on the image qualities, and/or reconstructing cardiac images based on the mean phase or phase of interest, thereby simplifying reconstruction processes, reducing the burden on a user for image quality evaluation or assessment, avoiding repeated image quality evaluation or assessment, reducing inconsistency in image processing due to, e.g., variations between assessments by different users, improving the efficiency of the image processing, improving the accuracy of the mean phase or phase of interest for cardiac image reconstruction, and/or further improving the quality of the reconstructed cardiac images.

In order to make the objects, technical solutions and advantages of the present disclosure clearer, the present disclosure will be further described in detail below with reference to the accompanying drawings and embodiments. It should be understood that the specific embodiments described herein are merely illustrative of the present disclosure and are not intended to limit the present disclosure.

A computed tomography (CT) device may include a gantry, a scanning bed, and a console for the physician to operate. A tube may be disposed on one side of the gantry, and detectors may be disposed on a side opposite to the tube. The console may include a computing device that controls CT scanning. The computing device may also be used to receive scan data collected by the detectors, process the scan data and reconstruct CT image(s). When scanning with CT, a patient may lie on the scanning bed, and the patient may be translated into the aperture of the gantry by the scanning bed. The tube disposed on the gantry may emit X-rays, and the X-rays may be received by the detectors to generate scan data. The scan data may be transmitted to the computing device, and the computing device may perform preliminary processing on the scan data and image reconstruction to obtain CT image(s).

It should be noted that a relative position, e.g., left, right, upper, lower, above, under or underneath, or the like, in the present disclosure may refer to the relative positions in the image(s). For example, an upper position in an image may be closer to the upper boundary of the image than the lower position; a lower position in the image may be closer to the lower boundary of the image than the upper position. A left position in an image may be closer to the left boundary of the image than the right position; a right position in an image may be closer to the right boundary of the image than the left position. Furthermore, the sagittal axis (also referred to as the Y axis) may refer to the horizontal line in the anterior to posterior direction, the coronal (frontal) axis (also referred to as the X axis) may refer to the horizontal line in the left (of the object) to right (of the object) direction, and the vertical axis (also referred to as the Z axis) may refer to the perpendicular line in the superior to inferior direction, which is perpendicular to the horizontal line. And the sagittal plane may refer to the tangent plane along with the sagittal axis and vertical axis, which may segment the object into left and right sections; the coronal (frontal) plane may refer to the tangent plane along with the coronal (frontal) axis and vertical axis, which may segment the object into anterior and posterior sections; and the transverse plane may refer to the tangent plane along with the sagittal axis and coronal (frontal) axis, which may segment the object into superior and inferior sections.

Figure 1:
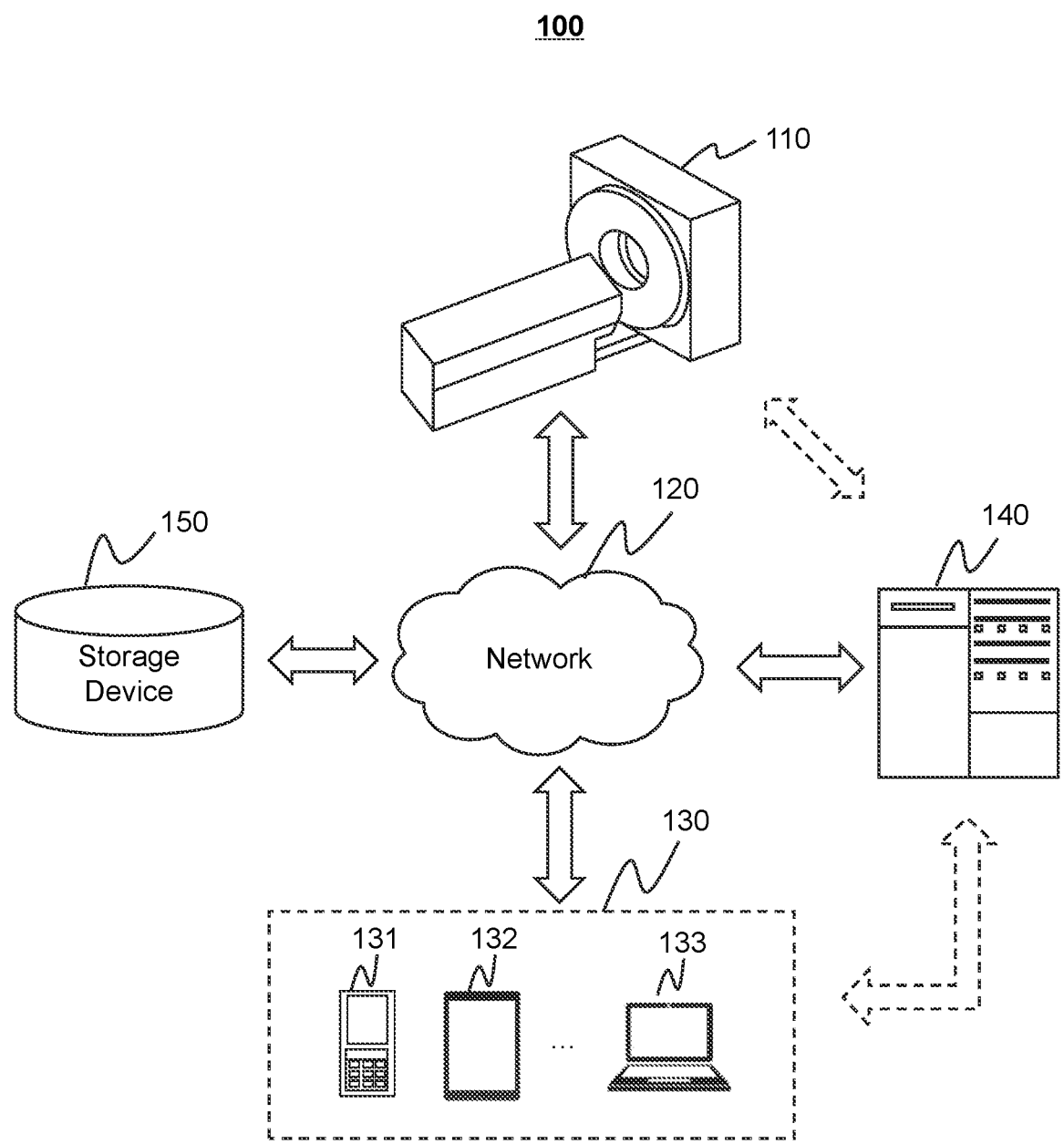
FIG. 1 is a schematic diagram illustrating an exemplary imaging system according to some embodiments of the present disclosure.

FIG. 1 is a schematic diagram illustrating an exemplary imaging system according to some embodiments of the present disclosure. As shown in FIG. 1, the imaging system 100 may include a scanner 110, a network 120, one or more terminals 130, a processing device 140, and a storage device 150. The components in the imaging system 100 may be connected in one or more of various ways. Merely by way of example, the scanner 110 may be connected to the processing device 140 through the network 120. As another example, the scanner 110 may be connected to the processing device 140 directly as indicated by the bi-directional arrow in dotted lines linking the scanner 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

The scanner 110 may scan an object and/or generate scan data relating to the object. In some embodiments, the scanner 110 may be a single-modality medical imaging device (e.g., a magnetic resonance imaging (MRI) device, a positron emission tomography (PET) device, a single-photon emission computed tomography (SPECT) device, a computed tomography (CT) device, or the like) or a multi-modality medical imaging device (e.g., a PET-MRI device, a SPECT-MRI device, or a PET-CT device). In some embodiments, the scanner 110 may include a gantry configured to imaging the object, a detection region configured to accommodate the object, and/or a scanning bed configured to support the object during an imaging process. The scanning bed may support the object during scanning. For example, the object may be supported and/or delivered to the detection region of the gantry by the scanning bed. In some embodiments, the scanner 110 may transmit image(s) via the network 120 to the processing device 140, the storage device 150, and/or the terminal(s) 130. For example, the image(s) may be sent to the processing device 140 for further processing or may be stored in the storage device 150.

In some embodiments, the object may be biological or non-biological. Merely by way of example, the object may include a patient, an organ, a tissue, a specimen, a man-made object, a phantom, etc. In some embodiments, the object to be scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

The network 120 may include any suitable network that can facilitate the exchange of information and/or data for the imaging system 100. In some embodiments, one or more components of the imaging system 100 (e.g., the scanner 110, the terminal 130, the processing device 140, the storage device 150, etc.) may communicate information and/or data with one or more other components of the imaging system 100 via the network 120. For example, the processing device 140 may obtain image data from the scanner 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanner 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage device 150 via the network 120. As another example, the processing device 140 may be directly connected to the scanner 110, the terminal 130 and/or the storage device 150 to access stored information and/or data. As a further example, the processing device 140 may process the data obtained from the scanner 110, evaluate image qualities, and/or reconstruct cardiac images. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140, or a portion of the processing device 140 may be integrated into the scanner 110.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include mass storage, removable storage, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the imaging system 100 (e.g., the processing device 140, the terminal 130, etc.). One or more components of the imaging system 100 may access the data or instructions stored in the storage device 150 via the network 120. In some embodiments, the storage device 150 may be directly connected to or communicate with one or more other components of the imaging system 100 (e.g., the processing device 140, the terminal 130, etc.). In some embodiments, the storage device 150 may be part of the processing device 140.

FIG. 2 is a schematic diagram illustrating exemplary hardware and software components of a computing device according to some embodiments of the present disclosure. The computing device 200 may be a general purpose computer or a special purpose computer; both may be used to implement an imaging system 100 of the present disclosure. In some embodiments, the processing device 140 may be implemented on the computing device 200, via its hardware, software program, firmware, or a combination thereof. Although only one such computer is shown, for convenience, the computer functions as described herein may be implemented in a distributed manner on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processor in accordance with techniques described herein. The computer instructions may include, for example, routines, programs, objects, components, data structures, procedures, modules, and functions, which perform particular functions described herein. For example, the processor 210 may obtain an image; determine, based on a maximum gray level of the plurality of elements of the image, one or more thresholds for segmenting the image; determine one or more sub-images of a region of interest by segmenting, based on the one or more thresholds, the image; and/or determine, based on the one or more sub-images of the region of interest, a quality index for the image.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal 130, the storage device 150, and/or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for scanning the heart of the object, a program for evaluating image qualities, and/or a program for reconstructing cardiac images.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the scanner 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
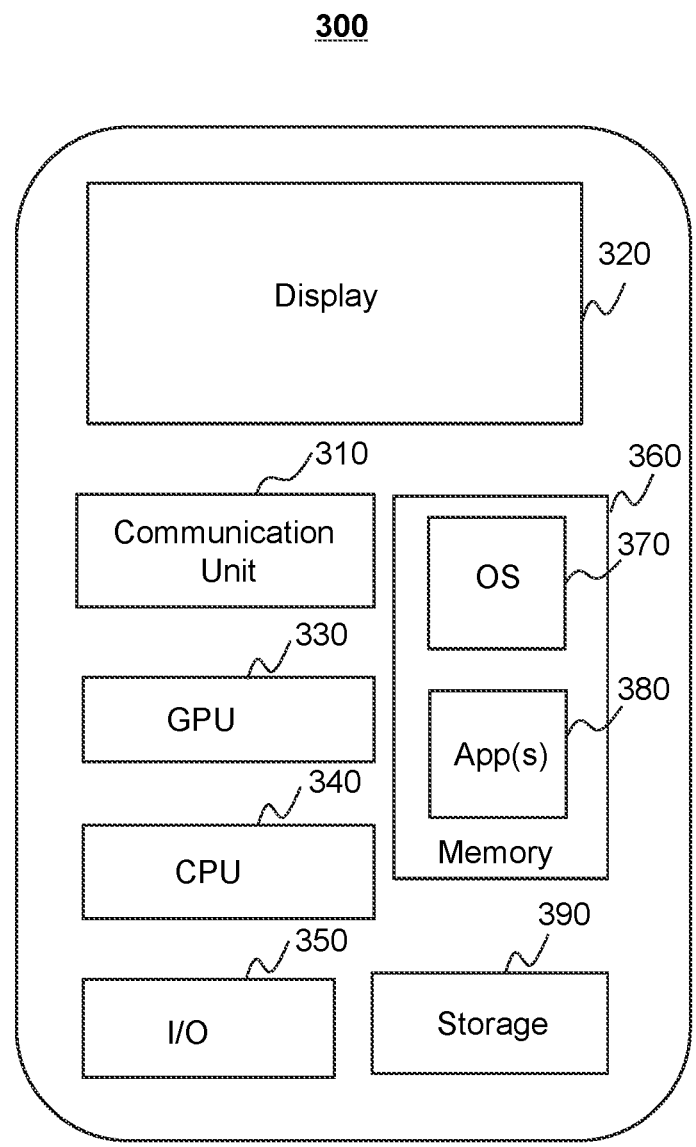
FIG. 3 is a schematic diagram illustrating exemplary hardware and/or software components of an exemplary mobile device that is configured to implement a specific system disclosed in the present disclosure.

FIG. 3 is a schematic diagram illustrating exemplary hardware and/or software components of an exemplary mobile device that is configured to implement a specific system disclosed in the present disclosure. As illustrated in FIG. 3, the mobile device 300 may include a communication unit 310, a display 320, a graphics processing unit (GPU) 330, a CPU 340, an I/O 350, a storage 390, and a memory 360. In some embodiments, any other suitable component, including but not limited to a system bus or a controller (not shown), may also be included in the mobile device 300. In some embodiments, a mobile operating system 370 (e.g., IOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120. In some embodiments, a user may input parameters to the imaging system 100, via the mobile device 300.

In order to implement various modules, units and their functions described above, a computer hardware platform may be used as hardware platforms of one or more elements (e.g., the processing device 140 and/or other components of the imaging system 100 described in FIG. 1). Since these hardware elements, operating systems and program languages are common; it may be assumed that persons skilled in the art may be familiar with these techniques and they may be able to provide information needed in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
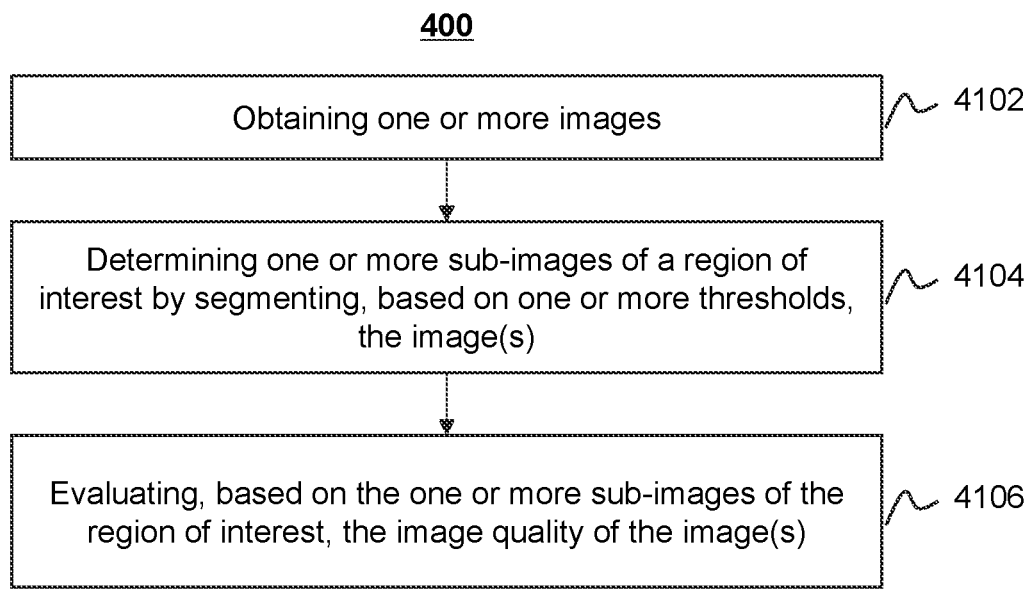
FIG. 4 is a flowchart illustrating an exemplary process for evaluating image quality according to some embodiments of the present disclosure.

FIG. 4 is a flowchart illustrating an exemplary process for evaluating image quality according to some embodiments of the present disclosure. In some embodiments, the process 400 may be executed by the imaging system 100. For example, the process 400 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 400 presented below are intended to be illustrative. In some embodiments, the process 400 may be accomplished with one or more additional operations not described, and/or without one or more of the operations discussed. Additionally, the order in which the operations of the process 400 as illustrated in FIG. 4 and described below is not intended to be limiting.

In some embodiments, as shown in FIG. 4, an exemplary image quality evaluation process is provided. The process 400 may include one or more of the following operations:

In 4102, one or more images (e.g., images to be evaluated) may be obtained.

In some embodiments, the processing device 140 (e.g., the obtaining module 13100) may perform operation 4102. In some embodiments, each image of the one or more images may include a plurality of elements. Each element of the plurality of elements may be a pixel or voxel. Each element may have a gray level. In some embodiments, the image(s) may be obtained from the scanner 110, the storage device 150, an external data source, etc. In some embodiments, the image(s) to be evaluated may be associated with an object (e.g., a patient) or a portion thereof. For example, cardiac image(s) to be evaluated may include elements relating to the thorax, the heart, one or more bones, one or more blood vessels, etc., of the object. In some embodiments, the image quality of an image may be evaluated based on one or more target portions of the image. In cardiac image reconstruction, the heart beats may produce motion artifacts into image(s), and the image quality may relate to one or more target portions of the object associated with heart beats (e.g., a ventricle, a blood vessel (e.g., a coronary artery)). It should be noted that in the following descriptions, image quality evaluation based on blood vessel(s) may be taken as an example for illustration purposes, any other target portion (e.g., a ventricle) may also be used as a reference for image quality evaluation. Besides, the operations illustrated below may also be used for the evaluation of other images (e.g., an abdomen image, a head image, a neck image, etc.). For illustration purposes, a target portion of the object may be referred to as a target object, and a target portion of an image may be referred to as a target region.

Specifically, in some embodiments, a plurality of images to be evaluated may be obtained, a maximum gray level of the plurality of images (or each of the plurality of images) may be determined, and/or the maximum gray level multiplied by one or more predetermined multiples may be designated as one or more thresholds for segmenting the images to be evaluated. In normal CT scanning, an object may be continuously scanned for a period of time, and corresponding scan data may be obtained. A plurality of images to be evaluated may be obtained based on the scan data. According to the obtained images to be evaluated, a maximum gray level of an image (or each image) may be determined, and/or the maximum gray level multiplied by one or more predetermined multiples may be designated as the threshold(s) for segmenting the image. In some embodiments, the number (or count) of the predetermined multiples may be no less than 1. In some embodiments, the predetermined multiples may be no larger than 1 (e.g., 0.1, 0.2, 0.3, 0.4, 0.5, etc.). In some embodiments, before the threshold(s) are determined, one or more operations may be performed on the image(s) to improve the resolution(s) of the image(s). Improvement of the resolution(s) may cause the improvement of the accuracy of determination of the blood vessel morphologies and/or the blood vessel boundaries. In some embodiments, the resolution(s) of the image(s) may be improved using a two-dimensional image interpolation algorithm.

In some embodiments, the threshold(s) for segmenting the images may also be referred to as segmentation threshold(s). In some embodiments, the resolution(s) of the image(s) may be improved based on one or more algorithms. Exemplary algorithms may include a machine learning algorithm, image super-resolution reconstruction algorithm, etc.

In 4104, one or more sub-images of a region of interest may be determined by segmenting, based on the one or more threshold(s), the image(s).

In some embodiments, the processing device 140 (e.g., the image of region of interest extraction module (or ROI image extracting module) 13200) may perform operation 4104. In some embodiments, a region of interest may refer to a target region in an image that has a relatively high correlation with or impact on the image quality. In some embodiments, the region of interest may include blood vessel(s), and accordingly, the sub-image(s) of the region of interest may include one or more blood vessels. In some embodiments, a sub-image of the region of interest (e.g., the blood vessel(s)) may also be referred to as a vascular image of interest.

In some embodiments, elements of an image (to be evaluated) with gray level(s) larger than (and/or equal to) a segmentation threshold may be extracted as a vascular image of interest corresponding to the segmentation threshold. In some embodiments, two or more vascular images of interest may be obtained by segmenting an image based on two or more segmentation thresholds. For example, three segmentation thresholds may be obtained according to the maximum gray level of an image multiplied by three predetermined multiples. In some embodiments, the image may be segmented based on a first segmentation threshold of the three segmentation thresholds. For example, a region of the image having elements with gray levels of greater than the first segmentation threshold may be designated as a first vascular image of interest. In some embodiments, the image may be segmented based on a second segmentation threshold of the three segmentation thresholds. For example, a region of the image having elements with gray levels greater than the second segmentation threshold may be designated as a second vascular image of interest. In some embodiments, the image may be segmented based on a third segmentation threshold of the three segmentation thresholds. For example, a region of the image having elements with gray levels greater than the third segmentation threshold may be designated as a third vascular image of interest.

It should be noted that the number of the segmentation thresholds and/or the vascular image of interest illustrated above is merely provided for the purposes of illustration, and not intended to limit the scope of the present disclosure.

In 4106, image quality (or qualities) of the image(s) may be evaluated based on the one or more sub-images of the region of interest.

In some embodiments, the processing device 140 (e.g., the image quality evaluation module 13300) may perform operation 4106. In some embodiments, the processing device 140 may determine a maximum quality index in the quality index(es) of the image(s); and/or designate an image that has the maximum quality index as a target image. The target image may have the optimal image quality among the image(s).

Specifically, in some embodiments, a quality index may be determined for an image (or each image) to be evaluated according to the vascular image(s) of interest corresponding to the image, image quality evaluation may be performed on the image according to the quality index of the image.

More specifically, in some embodiments, to determine the quality index of the image based on the vascular image(s) of interest corresponding to the image, the processing device 140 may determine a regularity degree of the image based on the vascular image(s) of interest. More specifically, in some embodiments, according to the vascular image(s) of interest, the perimeter and/or the area of a target region in the image to be evaluated may be determined. For example, if the target region includes a blood vessel, the perimeter and/or the area of the blood vessel in each vascular image of interest corresponding to the image to be evaluated may be determined. The perimeters (and/or the areas) of the blood vessels in the vascular images of interest corresponding to the image to be evaluated may be determined separately. In some embodiments, according to the perimeter(s) and/or the area(s) of the target region in the image to be evaluated, the regularity degree of the image to be evaluated may be determined. In some embodiments, according to the edge(s) of the vascular image(s) of interest, and/or the gradient map(s) of the vascular image(s) of interest, a sharpness degree of the image may be determined. In some embodiments, the quality index of each image may be determined according to the regularity degree of the image and/or the sharpness degree of the image. In some embodiments, the number of target regions (e.g., blood vessels) in different images may be inconsistent if the images are detected based on a same target object (e.g., at an identical physical position) but at different cardiac motion phases. In some embodiments, the image quality evaluation may need to be performed on the images (e.g., the images obtained in 4102) based on a same reference (or criteria), that is, the number of target regions (e.g., blood vessels) in the images that are detected based on a same target object (e.g., the blood vessels) at an identical physical position may need to be consistent. In some embodiments, a reference parameter (e.g., the number of basic blood vessels, or the number of blood vessels of a predetermined basic cardiac motion phase) may be introduced. The reference parameter may refer to a parameter configured to adjust the number (or count) of target regions to make the number (or count) of target regions (e.g., blood vessels) in the images that are detected based on a same target object (e.g., the blood vessels) at an identical physical position to be consistent. In some embodiments, according to the number of basic blood vessels and/or the numbers of blood vessels in the images to be evaluated, a regularity degree matrix of the images (to be evaluated) of each cardiac motion phase and a sharpness degree matrix of the images (to be evaluated) of each cardiac motion phase may be obtained. In some embodiments, the magnitudes of the regularity degree and the sharpness degree may be inconsistent. Therefore, it is desirable to adjust the regularity degree and the sharpness degree to a same baseline. In some embodiments, the regularity degree and/or the sharpness degree may be adjusted based on a weighting process, a normalization process, or the like, or a combination thereof.

For example, the processing device 140 may designate a weighted sum of the regularity degree and the sharpness degree as the quality index for the image. In some embodiments, each image of the image(s) obtained in 4102 may be evaluated similarly as illustrated above.

In some embodiments, the regularity degree of an image may relate to the morphology of the image. In some embodiments, the regularity degree may reflect an orderliness of the element(s) in an image to be evaluated. For example, the orderliness of a polygon may be lower than a circle, and accordingly, the regularity degree of the polygon may be lower than the circle. As another example, if an image has a relatively high level of artifact(s), i.e., the clarity of the boundary (or boundaries) of different regions in the image is relatively low, then the regularity degree of the image may be relatively low. In some embodiments, if an image has a relatively large regularity degree, the image may have a relatively high clarity (or quality) and/or a low level of artifacts. In some embodiments, the sharpness degree of an image may relate to the clarity of the edge(s) of a target region of the image. If the edge(s) of the target region is relatively clear, the sharpness degree of the image may be relatively large. If the edge(s) of the target region is relatively blurry (e.g., the image has a relatively high level of artifacts), the sharpness degree of the image may be relatively low. An image having a relatively large quality index may have a relatively high regularity degree, and/or a relatively high sharpness degree, and accordingly, the image may have a relatively fewer motion artifact, and/or a relatively high level of clarity. In some embodiments, if an image has a relatively large quality index, the image may have a relatively high image quality.

In some embodiments, image quality evaluation may be performed according to the quality indexes of the images to be evaluated, and the image having the largest quality index may be selected as a target image that has the optimum image quality.

In some embodiments, a plurality of images may be evaluated based on the evaluation process illustrated above. The quality indexes of the plurality of images may be determined. In some embodiments, the processing device 140 may determine one or more images having top N (in which N may be an integer larger than 0) quality indexes among the plurality of quality indexes as candidate target image(s). In some embodiments, the candidate target image(s) may be provided to a user (e.g., a doctor), and the user may select one or more target image(s) among the candidate target image(s). In some embodiments, the user may set a quality index threshold, and the processing device 140 may provide candidate target image(s) having quality indexes larger than or equal to the quality index threshold to the user for further determination of the target image(s). In some embodiments, the user may set the number N, and the processing device 140 may provide the candidate target image(s) having the top N quality indexes to the user for further determination of the target image(s).

According to the process for evaluating image quality described above, a maximum gray level (of an image) multiplied by one or more predetermined multiples may be designated as the thresholds for segmenting the image to be evaluated, and the image to be evaluated may be segmented based on the segmentation thresholds to obtain vascular image(s) of interest. According to the vascular image(s) of interest, the quality index of the image to be evaluated may be determined, and the image qualities of the images may be evaluated according to the quality indexes of the images. The automatic image quality evaluation of the image(s) based on the corresponding quality indexes of the image(s) may reduce the burden on the doctor for image quality evaluation, and further avoid repeated image reconstructions of a same image for image quality evaluation.

Figure 5:
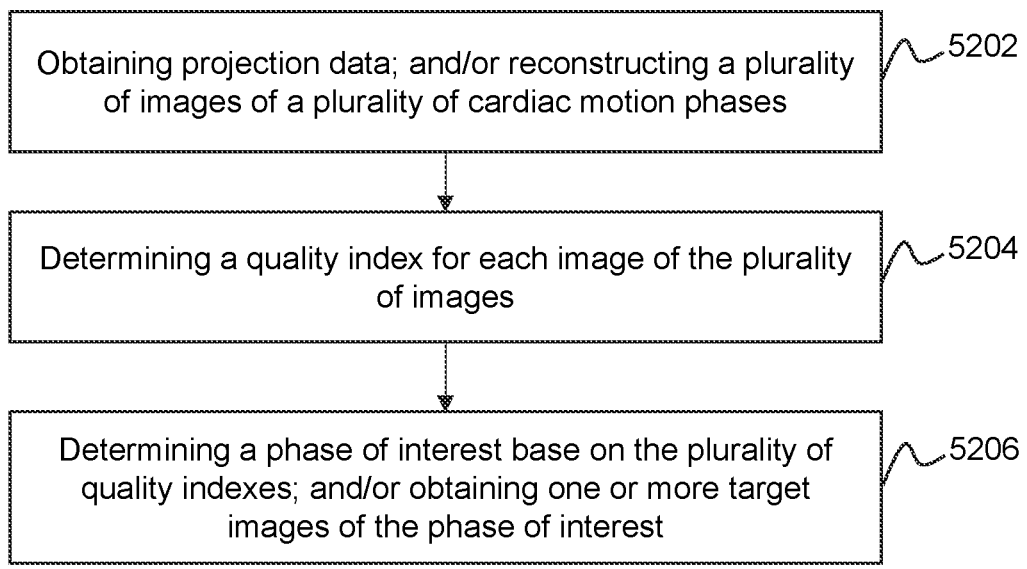
FIG. 5 is a flowchart illustrating an exemplary process for reconstructing an image according to some embodiments of the present disclosure.

FIG. 5 is a flowchart illustrating an exemplary process for reconstructing an image according to some embodiments of the present disclosure. In some embodiments, the process 500 may be executed by the imaging system 100. For example, the process 500 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In some embodiments, as shown in FIG. 5, an exemplary process for image reconstruction is provided. The process 500 may include one or more of the following operations:

In 5202, projection data of a plurality of cardiac motion phases may be obtained, and/or a plurality of images of the plurality of cardiac motion phases may be reconstructed based on the projection data. In some embodiments, the plurality of images of the plurality of cardiac motion phases may be determined as the images to be evaluated.

In some embodiments, the processing device 140 (e.g., the image selection module 13400) may perform operation 5202. The projection data may include a plurality of sub-sets of projection data. In some embodiments, a sub-set of projection data may correspond to a cardiac motion phase. In some embodiments, two or more sub-sets of projection data may correspond to a same cardiac motion phase. In some embodiments, the projection data may be generated by an imaging device (e.g., the scanner 110). In some embodiments, the imaging device may include a CT device. In some embodiments, the projection data may be obtained from the scanner 110, the storage device 150, an external data source, etc. In some embodiments, the processing device 140 may reconstruct a plurality of images corresponding to the plurality of cardiac motion phases based on the plurality of sub-sets of projection data corresponding to the plurality of cardiac motion phases. In some embodiments, the plurality of cardiac motion phases may include all discrete cardiac motion phases. In some embodiments, the plurality of cardiac motion phases may be sampled cardiac motion phases. In some embodiments, the images may be reconstructed using one or more reconstruction algorithms including, for example, Filtered Back-Projection (FBP), Algebraic Reconstruction Technique (ART), Local Reconstruction Algorithm (Local RA), and ordered-subset expectation maximization (OSEM), etc. In some embodiments, a cardiac motion phase may correspond to one or more images, while an image may correspond to one cardiac motion phase. In some embodiments, the images may be cardiac images.

In some embodiments, cardiac motion phases may be denoted by percentage values (e.g., percentage values between 0%-100%). A phase x % may correspond to a phase angle x %*360°. In some embodiments, the plurality of cardiac motion phases may be obtained at regular intervals (e.g., an interval of 1%, 2%, 5%, 10%, 15%, 20%, 25%, etc.). For example, regular intervals may be intervals of 3%, 6%, 9%, 12%, 15%, 18%, 21%, etc. In some embodiments, the plurality of sampled cardiac motion phases may be obtained at random intervals, irregular intervals, or by a certain preset rule which may be determined by a user or the imaging system 100. For example, the plurality of cardiac motion phases may be obtained at the random intervals from 1% to 100%. As another example, the plurality of sampled cardiac motion phases may be obtained at different intervals for different cardiac cycles. In some embodiments, a cardiac cycle may be divided into 100 phases from 1% to 100%. An exemplary regular interval of the cardiac motion phases may be 12.5%, and accordingly, 8 cardiac motion phases including 12.5%, 25%, 37.5%, 50%, 62.5%, 75%, 87.5%, and 100% may be obtained.

Specifically, in some embodiments, in normal CT scanning, an object may be continuously scanned for a period of time, and corresponding scan data (e.g., projection data) may be obtained. In a cardiac cycle, each phase (e.g., each discrete cardiac motion phase) may have corresponding scan data (e.g., projection data) obtained by CT scanning. In some embodiments, each cardiac motion phase of 100 phases within 1%-100% in each cardiac cycle may have corresponding scan data. The images of the corresponding phases may be reconstructed based on the projection data of the cardiac motion phases, respectively. In some embodiments, image reconstruction may be performed based on a relatively small reconstruction matrix and/or a relatively large layer thickness, but the images (reconstructed based on the relatively small reconstruction matrix and/or the relatively large layer thickness) may have a relatively low resolution, and may have a negative impact on subsequent segmentation operation(s). In some embodiments, a relatively accurate reconstruction may be performed based on a reconstruction center (that is automatically determined in the region of interest (e.g., blood vessel(s))), a relatively small field of view (FOV), and/or a relatively large layer thickness. In some embodiments, a mean phase may be determined based on the images corresponding to the plurality of cardiac motion phases. Images of cardiac motion phases in a preset range including the mean phase may be selected, and images of the region of interest may be extracted in the selected images. In some embodiments, a blood vessel centerline may be extracted in an image of the region of interest. In some embodiments, image segmentation may be performed on the image(s) based on a preset region centered at the blood vessel centerline, and a plurality of images to be evaluated may be obtained.

More descriptions of the reconstruction center and/or the reconstruction based on a relatively small field of view (FOV) may be found in Chinese Patent Application No. 201810597965.1 entitled "METHODS, SYSTEMS, AND COMPUTING DEVICES FOR CARDIAC IMAGE RECONSTRUCTION," filed on Jun. 11, 2018, and U.S. application Ser. No. 16/437,003, entitled "SYSTEMS AND METHODS FOR RECONSTRUCTING CARDIAC IMAGES," filed on even date, the contents of which are hereby incorporated by reference.

In some embodiments, the mean phase may refer to a relatively optimal phase (in which the cardiac motion is relatively slight) for a plurality of cardiac cycles (in which the projection data of the object are generated). In some embodiments, cardiac images of the mean phase may have a relatively low level of motion artifacts, a relatively high quality, and/or a relatively high clarity. More descriptions of the determination of the mean phase may be found elsewhere in the present disclosure (e.g., FIGS. 6-7 and descriptions thereof), or Chinese Patent Application No. 201811133622.6 entitled "METHODS, SYSTEMS, COMPUTING DEVICES, AND READABLE STORAGE MEDIA FOR CARDIAC IMAGE RECONSTRUCTION," filed on Sep. 27, 2018, and Chinese Patent Application No. 201811133609.0 entitled "METHODS, SYSTEMS, COMPUTING DEVICES, AND READABLE STORAGE MEDIA FOR CARDIAC IMAGE RECONSTRUCTION," filed on Sep. 27, 2018, and U.S. application Ser. No. 16/437,003, entitled "SYSTEMS AND METHODS FOR RECONSTRUCTING CARDIAC IMAGES," filed on even date, the contents of which are hereby incorporated by reference. More descriptions of the determination of the images to be evaluated may be found elsewhere in the present disclosure (e.g., FIG. 6 and descriptions thereof).

In 5204, a quality index of each image of the plurality of images may be determined.

In some embodiments, the processing device 140 (e.g., the quality index determination module 13500) may perform operation 5204. In some embodiments, operation 5204 may be performed according to one or more operations (e.g., operations 4104 and 4106) described in FIG. 4. More descriptions of the determination of the quality index may be found elsewhere in the present disclosure (e.g., FIG. 12 and descriptions thereof).

Specifically, in some embodiments, a maximum gray level of the images (or each image) to be evaluated may be determined, and/or the maximum gray level multiplied by one or more predetermined multiples may be designated as segmentation thresholds. According to the segmentation thresholds, each image may be segmented to obtain a plurality of vascular images of interest. A quality index of each image to be evaluated may be determined according to the vascular images of interest obtained from the image. Therefore, in each cardiac cycle, a plurality of quality indexes of the images (to be evaluated) of the plurality of cardiac motion phases may be obtained.

In 5206, a phase of interest may be determined based on the plurality of quality indexes, and/or one or more target images of the phase of interest may be obtained.

In some embodiments, the processing device 140 (e.g., the image reconstruction module 13600) may perform operation 5206. In some embodiments, the processing device 140 may determine a maximum quality index in the plurality of quality indexes (in each cardiac cycle), and designate the phase of an image that has the maximum quality index as the phase of interest.

The phase of interest may refer to a relatively optimal phase (in which the cardiac motion is relatively slight) for each cardiac cycle. The phases of interest for different cardiac cycles may be the same or different. The phase of interest may be the same as or different from the mean phase. For example, a phase of interest in a first cardiac cycle may be the same as the mean phase. As another example, a phase of interest in a second cardiac cycle may be less than the mean phase. As a further example, a phase of interest in a third cardiac cycle may be larger than the mean phase. More descriptions of the determination of the phase of interest may be found elsewhere in the present disclosure (e.g., FIG. 6 and descriptions thereof), or Chinese Patent Application No. 201811133622.6 entitled "METHODS, SYSTEMS, COMPUTING DEVICES, AND READABLE STORAGE MEDIA FOR CARDIAC IMAGE RECONSTRUCTION," filed on Sep. 27, 2018, and Chinese Patent Application No. 201811133609.0 entitled "METHODS, SYSTEMS, COMPUTING DEVICES, AND READABLE STORAGE MEDIA FOR CARDIAC IMAGE RECONSTRUCTION," filed on Sep. 27, 2018, and U.S. application Ser. No. 16/437,003, entitled "SYSTEMS AND METHODS FOR RECONSTRUCTING CARDIAC IMAGES," filed on even date, the contents of which are hereby incorporated by reference.

Specifically, in some embodiments, in each cardiac cycle, the image that has the maximum quality index may be selected, and accordingly, the phase of the image that has the maximum quality index in the cardiac cycle may be determined as the phase of interest in the cardiac cycle. In some embodiments, an image reconstructed at the phase of interest may be determined as a target cardiac image of the phase of interest (in the cardiac cycle). In some embodiments, images of the plurality of cardiac motion phases may be reconstructed based on the projection data of the plurality of cardiac motion phases, the image with the maximum quality index may be selected, and the phase of the image with the maximum quality index may be determined as the phase of interest. In some embodiments, the reconstructed image of the phase of interest may be selected as the target image of the phase of interest. In some embodiments, the image with the maximum quality index may be directly selected as the target image of the phase of interest.

In some embodiments, in order to determine the mean phase or phase of interest, images to be evaluated may be reconstructed based on projection data and a reconstruction center (that is automatically determined in the region of interest (e.g., blood vessel(s))), a relatively small field of view (FOV), and/or a relatively large layer thickness, thereby reducing the amount of data involved in computation, saving computing resources, and/or improving processing efficiency. In some embodiments, after the mean phase or phase of interest is determined, image(s) may be reconstructed based on a regular reconstruction center (e.g., the rotation center of the scanner 110), a relatively large FOV, and/or a relatively small layer thickness, and accordingly, the reconstructed images may have more detail information, thereby facilitating the diagnosis of diseases.

According to the process described above, image reconstruction may be performed based on projection data of the plurality of cardiac motion phases to obtain images of the plurality of cardiac motion phases. The image(s) to be evaluated of a specific phase may be obtained from all the images corresponding to the plurality of cardiac motion phases. According to one or more image quality evaluation rules, the quality index of each image to be evaluated may be determined, the phase of interest may be determined according to the quality indexes of images to be evaluated of the plurality of cardiac motion phases, and the target image(s) of the phase of interest may be reconstructed. The operations illustrated above does not rely on user interface interaction, and can automatically detect and extract the images to be evaluated, and automatically analyze the image quality of the images (e.g., vascular images). In coronary angiography, the process can be performed to automatically select the phase of interest. Users (e.g., doctors) are not required to evaluate image(s) and choose one or more phases of interest for image reconstruction. Therefore, the coronary reconstruction process may be simplified, and the users' time to evaluate image(s) and/or select parameters (e.g., the phase of interest) may be saved.

It should be noted that the above description of process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 5202 may be decomposed into two operations, in which a first operation may obtain projection data, and a second operation may reconstruct the plurality of images of the plurality of cardiac motion phases. As another example, operation 5206 may be decomposed into two operations, in which a first operation may determine the phase of interest, and a second operation may obtain target image(s) of the phase of interest.

Figure 6:
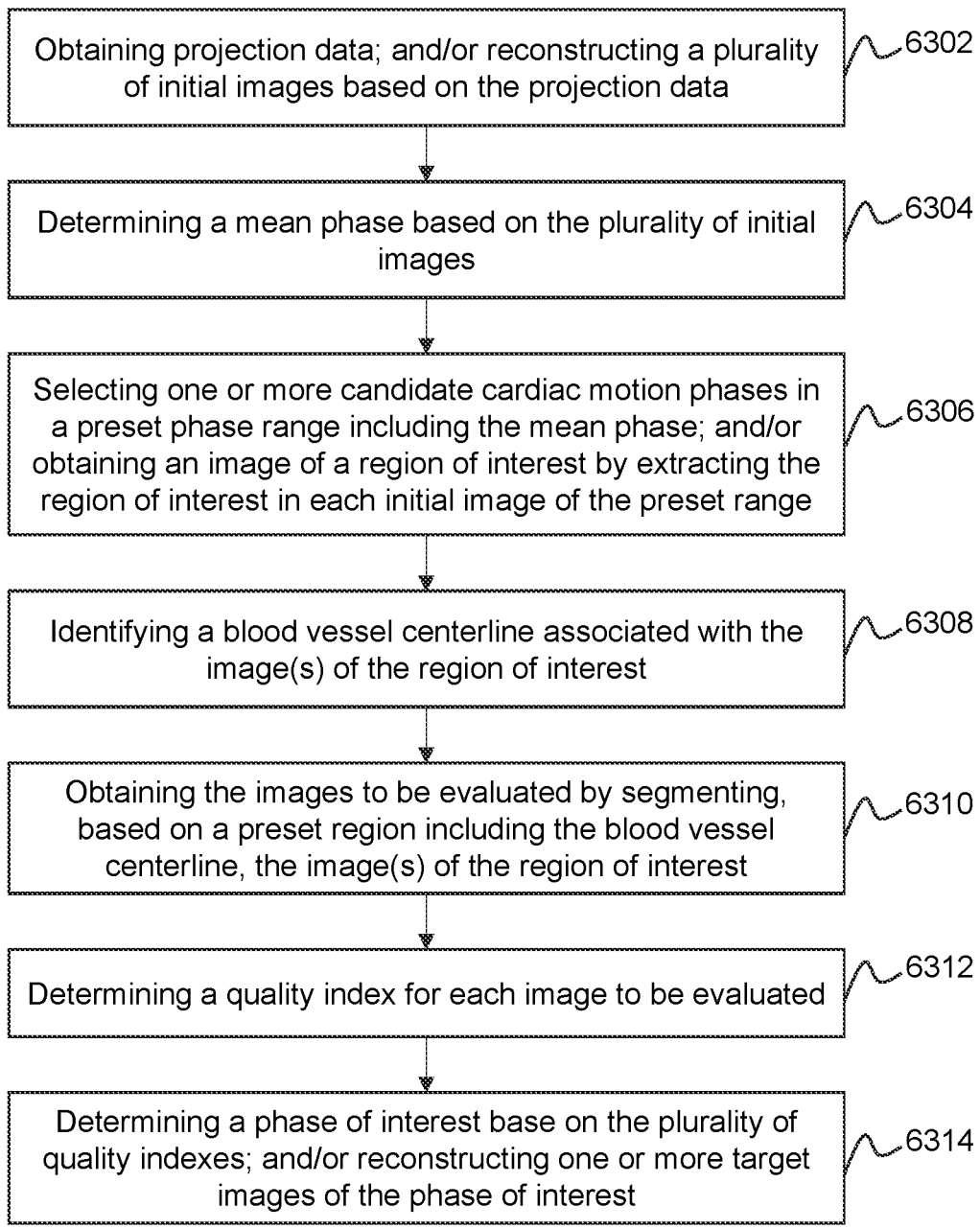
FIG. 6 is another flowchart illustrating an exemplary process for reconstructing an image according to some embodiments of the present disclosure.

FIG. 6 is another flowchart illustrating an exemplary process for reconstructing an image according to some embodiments of the present disclosure. In some embodiments, the process 600 may be executed by the imaging system 100. For example, the process 600 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 5202 of FIG. 5 may be performed according to one or more operations of the process 600 in FIG. 6.

In some embodiments, as shown in FIG. 6, an exemplary process for image reconstruction is provided. The process 600 may include one or more of the following operations:

In 6302, projection data of a plurality of cardiac motion phases may be obtained, and/or a plurality of initial images may be reconstructed based on the projection data.

In some embodiments, the processing device 140 (e.g., the image selection module 13400) may perform operation 6302. The projection data may include a plurality of sub-sets of projection data. In some embodiments, a sub-set of projection data may correspond to a cardiac motion phase. In some embodiments, two or more sub-sets of projection data may correspond to a same cardiac motion phase. In some embodiments, the projection data may be generated by an imaging device (e.g., the scanner 110). In some embodiments, the imaging device may include a CT device. In some embodiments, the projection data may be obtained from the scanner 110, the storage device 150, an external data source, etc. In some embodiments, the plurality of cardiac motion phases may include all the cardiac motion phases. In some embodiments, the plurality of cardiac motion phases may be sampled cardiac motion phases. In some embodiments, the plurality of initial images may include cardiac images. In some embodiments, one or more initial images may correspond to a same cardiac motion phase. In some embodiments, one or more cardiac images to be evaluated may be selected from the plurality of initial images.

Specifically, in some embodiments, in normal CT scanning, an object may be continuously scanned for a period of time, and corresponding scan data (e.g., projection data) may be obtained. In a cardiac cycle, each phase (e.g., each discrete cardiac motion phase) may have corresponding scan data (e.g., projection data) obtained by CT scanning. In some embodiments, each cardiac motion phase of 100 phases within 1%-100% in each cardiac cycle may have corresponding scan data. The initial images of the corresponding phases may be reconstructed based on the projection data of the plurality of cardiac motion phases, respectively.

In some embodiments, as illustrated above, image reconstruction may be performed based on a relatively small reconstruction matrix and/or a relatively large layer thickness.

In 6304, a mean phase may be determined based on the plurality of initial images.

In some embodiments, the processing device 140 (e.g., the image selection module 13400) may perform operation 6304.

Specifically, in some embodiments, cardiac motion parameters of the plurality of cardiac motion phases may be determined according to the initial images of the plurality of cardiac motion phases. The mean phase may be determined according to the cardiac motion parameters of the plurality of cardiac motion phases. The mean phase may include a mean phase of a systolic period, and/or a mean phase of a diastolic period.

In some embodiments, the processing device 140 may determine a cardiac motion parameter corresponding to each cardiac motion phase of the plurality of cardiac motion phases based on an initial cardiac image of the plurality of initial cardiac images. The processing device 140 may determine the mean phase based on the plurality of cardiac motion parameters corresponding to the plurality of cardiac motion phases. In some embodiments, a cardiac motion parameter may refer to a parameter describing the cardiac motion. In some embodiments, the cardiac motion parameter may be associated with a cardiac motion rate or intensity. Exemplary cardiac motion parameters may include a cardiac motion rate, a cardiac motion intensity, etc. The cardiac motion rate may include a blood flow rate in a blood vessel of the heart, a muscle contraction rate of a cardiac muscle, etc. The cardiac motion intensity may include a magnitude of vasoconstriction, a magnitude of vasodilation, a heartbeat amplitude, etc. In some embodiments, the cardiac motion parameter may refer to a parameter associated with the cardiac motion rate or the cardiac motion intensity. For example, the parameter may be the cardiac motion rate (or the cardiac motion intensity) multiplied by a coefficient. As another example, the parameter may relate to a reciprocal of the cardiac motion rate (or the cardiac motion intensity). In some embodiments, if the cardiac motion parameter is relatively large, the cardiac motion may be relatively pronounced. In some embodiments, if the cardiac motion parameter is relatively small, the cardiac motion may be relatively pronounced. More descriptions of the determination of the cardiac motion parameters may be found elsewhere in the present disclosure (e.g., FIG. 7 and descriptions thereof), or Chinese Patent Application No. 201811133622.6 entitled "METHODS, SYSTEMS, COMPUTING DEVICES, AND READABLE STORAGE MEDIA FOR CARDIAC IMAGE RECONSTRUCTION," filed on Sep. 27, 2018, and Chinese Patent Application No. 201811133609.0 entitled "METHODS, SYSTEMS, COMPUTING DEVICES, AND READABLE STORAGE MEDIA FOR CARDIAC IMAGE RECONSTRUCTION," filed on Sep. 27, 2018, and U.S. application Ser. No. 16/437,003, entitled "SYSTEMS AND METHODS FOR RECONSTRUCTING CARDIAC IMAGES," filed on even date, the contents of which are hereby incorporated by reference.

In 6306, one or more candidate cardiac motion phases in a preset phase range may be selected, and/or an image of a region of interest may be obtained by extracting the region of interest in each initial image of the preset phase range. In some embodiments, the preset range may include the mean phase.

In some embodiments, the processing device 140 (e.g., the image selection module 13400) may perform operation 6306. In some embodiments, the region of interest may include blood vessel(s), and accordingly, an image of the region of interest may refer to a vascular image of interest. In some embodiments, before extracting the region of interest in the initial image(s) of the preset range, the initial image(s) may be smoothed (e.g., using a low-pass filter) to facilitate further processing. Exemplary low-pass filters may include a Butterworth filter, a Chebyshev filter, a Gaussian filter, etc.

In some embodiments, the cardiac motion phases selected in the preset range may include part or all of the phases in the preset range. For example, if the mean phase is 45%, and the preset range is 40%-50%, then the cardiac motion phase(s) in the preset range 40%-50% may be selected (e.g., 41%, 42%, 43%, 44%, 45%, 46%, 47%, 48%, 49%, 50%).

In some embodiments, the preset range may be 5%, 10%, 20% (or the like) around the mean phase. For example, in each cardiac cycle, phases within 10% around the mean phase may be selected, and images corresponding to the phases within 10% around the mean phase in each cardiac cycle may be reconstructed. Merely by way of example, if the mean phase is M %, and the preset range is 2N %, then the cardiac motion phases from (M−N) % to (M+N) % (i.e., phases within 2N % around the mean phase) may be selected.

Specifically, in some embodiments, the initial image(s) in the preset phase range including the mean phase may be selected, and/or the selected initial image(s) in the preset range may be smoothed by the Gaussian low-pass filter. In some embodiments, a ventricular image may be extracted from a smoothed image. A threshold associated with gray level(s) of a contrast agent (in the plurality of initial images) may be determined based on one or more ventricular images. Image segmentation may be performed on the ventricular image(s) according to the threshold associated with the gray level of the contrast agent to obtain one or more contrast agent images. In some embodiments, and an image of the region of interest may be determined based on a contrast agent image.

More descriptions of the determination of the image(s) of the region of interest may be found elsewhere in the present disclosure (e.g., FIG. 8 and descriptions thereof), or Chinese Patent Application No. 201811133622.6 entitled "METHODS, SYSTEMS, COMPUTING DEVICES, AND READABLE STORAGE MEDIA FOR CARDIAC IMAGE RECONSTRUCTION," filed on Sep. 27, 2018, and Chinese Patent Application No. 201811133609.0 entitled "METHODS, SYSTEMS, COMPUTING DEVICES, AND READABLE STORAGE MEDIA FOR CARDIAC IMAGE RECONSTRUCTION," filed on Sep. 27, 2018, and U.S. application Ser. No. 16/437,003, entitled "SYSTEMS AND METHODS FOR RECONSTRUCTING CARDIAC IMAGES," filed on even date, the contents of which are hereby incorporated by reference.

In 6308, a blood vessel centerline associated with the image(s) of the region of interest may be identified according to the image(s) of the region of interest obtained in 6306.

In some embodiments, the processing device 140 (e.g., the image selection module 13400) may perform operation 6308. More descriptions of the blood vessel centerline and the identification of the blood vessel centerline may be found elsewhere in the present disclosure (e.g., FIG. 10 and descriptions thereof).

Specifically, in some embodiments, one or more images in a coronal plane and/or one or more images in a sagittal plane may be generated based on the image(s) of the region of interest. In some embodiments, a blood vessel main body may be determined according to the image(s) in the coronal plane and/or the image(s) in the sagittal plane. In some embodiments, one or more false positive vessels may be filtered out from the blood vessel main body. In some embodiments, the position of a blood vessel center in each transverse layer associated with the image(s) of the region of interest may be determined, and accordingly, the blood vessel centerline associated with the image(s) of the region of interest may be obtained based on the position of the blood vessel center in the each transverse layer.

In 6310, the images to be evaluated may be obtained by segmenting, based on a preset region including the blood vessel centerline, the image(s) of the region of interest.

In some embodiments, the processing device 140 (e.g., the image selection module 13400) may perform operation 6310. In some embodiments, the preset region may be centered at the blood vessel centerline.

Specifically, in some embodiments, a top-hat transformation may be performed on each image of the region of interest to obtain a transformed image of the region of interest. The transformed image of the region of interest may mainly include information of a target object (e.g., a blood vessel). According to a threshold associated with gray level(s) of soft tissue(s), the (transformed) image(s) of the region of interest may be segmented to obtain image(s) that reserve the intraventricular region. In some embodiments, elements of the image(s) that reserve the intraventricular region and within a preset region including the blood vessel centerline may be extracted as the image(s) to be evaluated.

Figure 11:
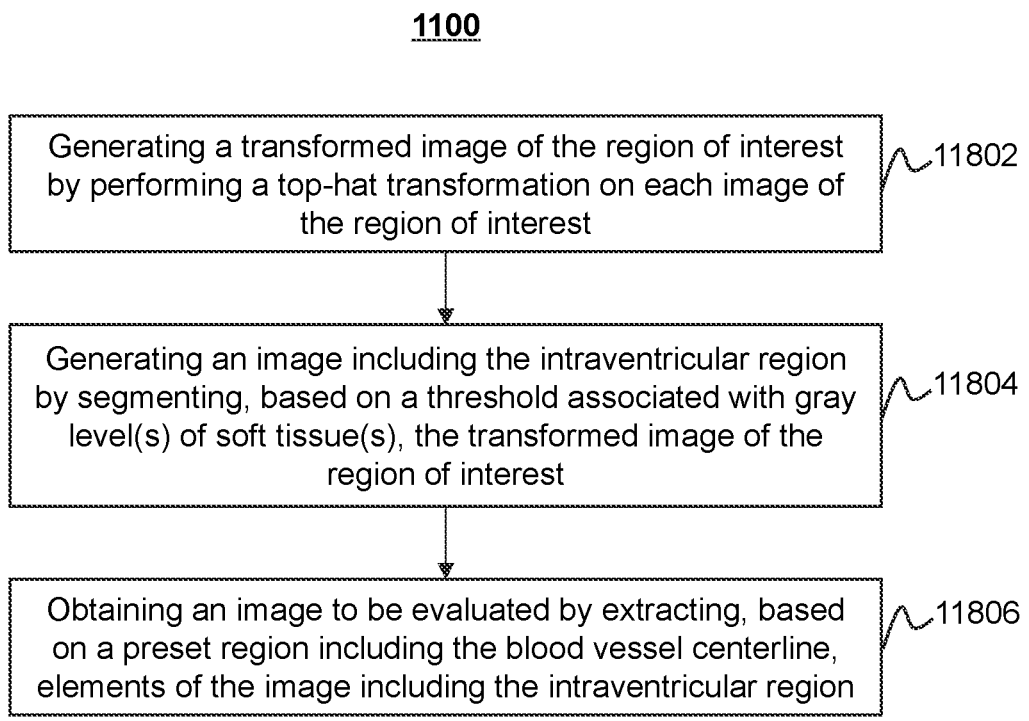
FIG. 11 is a flowchart illustrating an exemplary process for determining image(s) to be evaluated according to some embodiments of the present disclosure.

More descriptions of the determination of the images to be evaluated may be found elsewhere in the present disclosure (e.g., FIG. 11 and descriptions thereof).

In 6312, the quality index for each image to be evaluated may be determined. In some embodiments, the quality index(es) may be determined based on one or more image quality evaluation rules described in the present disclosure.

In some embodiments, the processing device 140 (e.g., the quality index determination module 13500) may perform operation 6312. In some embodiments, operation 6312 may be performed similarly to the operations 4104 and/or 4106.

Specifically, in some embodiments, a maximum gray level of the images (or each image) to be evaluated may be determined, and/or the maximum gray level multiplied by one or more predetermined multiples may be designated as segmentation thresholds. According to the segmentation thresholds, each image may be segmented to obtain a plurality of vascular images of interest. A quality index of each image to be evaluated may be determined according to the vascular images of interest obtained from the image. Therefore, in each cardiac cycle, a plurality of quality indexes of the images (to be evaluated) of the plurality of cardiac motion phases may be obtained.

In 6314, a phase of interest may be determined based on the plurality of quality indexes of the images to be evaluated, and/or one or more target images of the phase of interest may be reconstructed.

In some embodiments, the processing device 140 (e.g., the image reconstruction module 13600) may perform operation 6314.

Specifically, in some embodiments, in each cardiac cycle, the image (to be evaluated) that has the maximum quality index may be selected, and accordingly, the phase of the image that has the maximum quality index in the cardiac cycle may be determined as the phase of interest in the cardiac cycle. In some embodiments, an image reconstructed at the phase of interest may be determined as a target cardiac image of the phase of interest (in the cardiac cycle).

In some embodiments, the processing device 140 may select the one or more target cardiac images of the phase of interest from the plurality of cardiac images; or reconstruct the one or more target cardiac images of the phase of interest based on one or more sub-sets of projection data corresponding to the phase of interest.

According to the process for image reconstruction described above, the interference(s) of cardiac motion may be eliminated from the target cardiac image(s). The region of interest may be used as the image to be evaluated, and thus, the automatic evaluation may be performed more accurately, further improving the accuracy of automatic evaluation, and saving the time of doctors in parameter selection for image quality evaluation.

It should be noted that the above description of process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 6302 may be decomposed into two operations, in which a first operation may obtain projection data, and a second operation may reconstruct the plurality of initial images. As another example, operation 6306 may be decomposed into two operations, in which a first operation may select candidate cardiac motion phases, and a second operation may obtain image(s) the region of interest. As a further example, operation 6314 may be decomposed into two operations, in which a first operation may determine a phase of interest, and a second operation may reconstruct target image(s) of the phase of interest.

Figure 7:
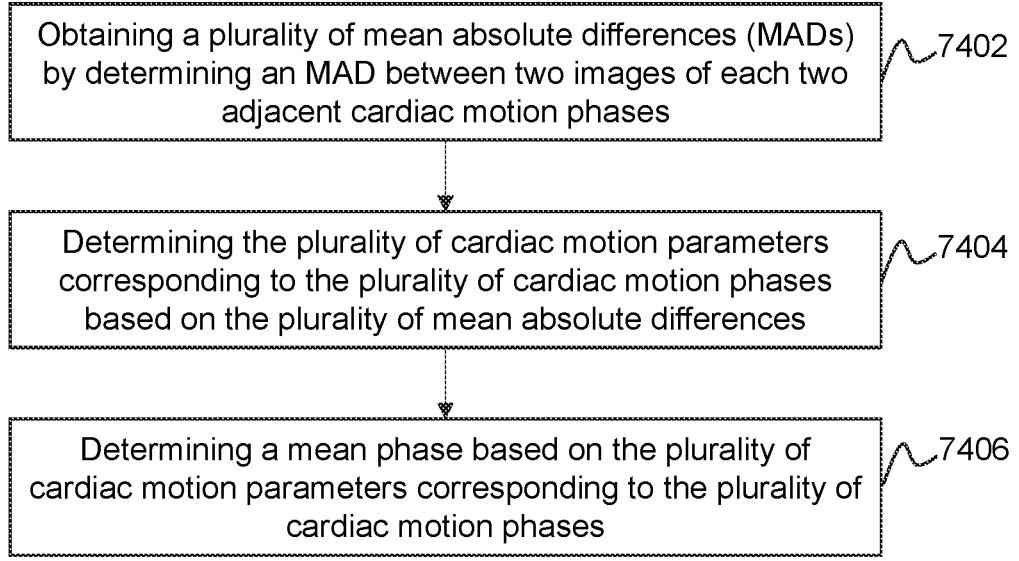
FIG. 7 is a flowchart illustrating an exemplary process for determining a mean phase according to some embodiments of the present disclosure.

FIG. 7 is a flowchart illustrating an exemplary process for determining a mean phase according to some embodiments of the present disclosure. In some embodiments, the process 700 may be executed by the imaging system 100. For example, the process 700 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, operation 6304 of FIG. 6 may be performed according to one or more operations of the process 700 in FIG. 7.

In some embodiments, as shown in FIG. 7, an exemplary process for determining a mean phase is provided. The process 700 may include one or more of the following operations:

In 7402, a plurality of mean absolute differences (MADs) may be obtained by determining an MAD between two images of each two adjacent cardiac motion phases. In some embodiments, an MAD between two images of each two adjacent cardiac motion phases may be determined based on the values of the elements of the two images and/or the sizes of the two images.

In some embodiments, the processing device 140 (e.g., the image selection module 13400) may perform operation 7402.

Specifically, in some embodiments, in cardiac image reconstruction, the cardia motion phases may range from 1% to 100%. In some embodiments, if image evaluation is performed on images of all phases, the image evaluation efficiency may be relatively low. Therefore, it may be desirable to set a phase range in which image evaluation may be performed. In some embodiments, it may be required that the blood vessel(s) in the three-dimensional image(s) (e.g., obtained by multi-planar reconstruction) are continuous. If an excessive phase range is set, the target region(s) in a series of target images of the phase of interests in different cardiac cycles may be discontinuous.

In some embodiments, the mean phase may be determined according to clinical experience values. For example, the mean phase in the systolic period may be set as 45%, and the mean phase in the diastolic period may be set as 75%.

In some embodiments, the mean phase may be determined according to the images. In some embodiments, before determining the mean absolute differences, the images corresponding to the plurality of cardiac motion phases may be pre-processed. In some embodiments, the preprocessing may include: performing image segmentation on the images of the plurality of cardiac motion phases according to one or more thresholds; and removing one or more regions that are unrelated to cardiac motion to obtain images of one or more regions relating to cardiac motion.

In some embodiments, the plurality of cardiac motion phases may be sampled cardiac motion phases. More descriptions of the sampled cardiac motion phases may be found in Chinese Patent Application No. 201811133622.6 entitled "METHODS, SYSTEMS, COMPUTING DEVICES, AND READABLE STORAGE MEDIA FOR CARDIAC IMAGE RECONSTRUCTION," filed on Sep. 27, 2018, and Chinese Patent Application No. 201811133609.0 entitled "METHODS, SYSTEMS, COMPUTING DEVICES, AND READABLE STORAGE MEDIA FOR CARDIAC IMAGE RECONSTRUCTION," filed on Sep. 27, 2018, and U.S. application Ser. No. 16/437,003, entitled "SYSTEMS AND METHODS FOR RECONSTRUCTING CARDIAC IMAGES," filed on even date, the contents of which are hereby incorporated by reference.

In some embodiments, the MAD between the two images of the each two adjacent cardiac motion phases may be determined as:

$$MAD(A, B) = \frac{1}{matrix \cdot \wedge 2} \sum_{i}^{matrix} \sum_{j}^{matrix} |A(i, j) - B(i, j)|, \quad (1)$$

where A and B represent the (cardiac) images of the each two adjacent cardiac motion phases, respectively; $A(i, j)$ is the gray level of a pixel with a coordinate $(i, j)$ in the image A; $B(i, j)$ is the gray level of a pixel with a coordinate $(i, j)$ in the image B; matrix is the size of the image matrix A and/or B; $MAD(A, B)$ is the mean absolute difference between images A and B.

In 7404, the plurality of cardiac motion parameters corresponding to the plurality of cardiac motion phases may be determined based on the plurality of MADs.

In some embodiments, the processing device 140 (e.g., the image selection module 13400) may perform operation 7404.

Specifically, in some embodiments, an MAD between an image of a cardiac motion phase and another image of a previous cardiac motion phase may be obtained as a first parameter. In some embodiments, an MAD between an image of a cardiac motion phase and an image of a next cardiac motion phase may be obtained as a second parameter. In some embodiments, the first parameter and the second parameter of the same image may be added to obtain a cardiac motion parameter of the cardiac motion phase.

In some embodiments, the processing device 140 may determine a first MAD between a first cardiac image of a first cardiac motion phase that occurs before the cardiac motion phase and a cardiac image of the cardiac motion phase. In some embodiments, the processing device 140 may determine a second MAD between a second cardiac image of a second cardiac motion phase that occurs after the cardiac motion phase and the cardiac image of the cardiac motion phase. In some embodiments, the processing device 140 may further designate a sum of the first MAD and the second MAD as the cardiac motion parameter corresponding to the cardiac motion phase. In some embodiments, the first cardiac motion phase may be adjacent to the cardiac motion phase. In some embodiments, the second cardiac motion phase may be adjacent to the cardiac motion phase. In some embodiments, the cardiac motion phases (in a same cycle or different cycles) may be arranged based on their respective sequence numbers, e.g., in an ascending order. The sequence number of a cardiac motion phase may be determined based on the timing of the cardiac motion phase in the cycle in which the cardiac motion phase occurs relative to a reference time point of the cycle. Exemplary reference time points of a cycle of the cardiac motion may include the beginning of the cardiac cycle (e.g., the time of contraction of the atria), the end of the cardiac cycle (e.g., the time of ventricular relaxation), or a midpoint of the cardiac cycle (e.g., the beginning of the ventricular systole). Cardiac motion phases that occur in different cycles of cardiac motion may have a same sequence number. If a sequence number of a cardiac motion phase A is lower than a sequence number of a cardiac motion phase B, then the cardiac motion phase A may be considered "occur before" the cardiac motion phase B, and accordingly, the cardiac motion phase B may "occur after" the cardiac motion phase A. If the absolute value of a difference between sequence numbers of two cardiac motion phases C and D is 1, then the cardiac motion phase C and the cardiac motion phase D may be considered "adjacent to" each other.

In some embodiments, the determination of the cardiac motion parameter of a cardiac motion phase may be represented as:

$$\Delta M(P_l, k) = MAD(V_k(P_l, i, j), V_k(P_{l-1}, i, j)) + MAD(V_k(P_l, i, j), V_k(P_{l+1}, i, j)), \quad (2)$$

where $MAD(V_k(P_l, i, j), V_k(P_{l-1}, i, j))$ is the mean absolute difference between a cardiac image $V_k(P_l, i, j)$ of a current cardiac motion phase and a cardiac image $V_k(P_{l-1}, i, j)$ of a cardiac motion phase that occurs before the current cardiac motion phase; $MAD(V_k(P_l, i, j), V_k(P_{l+1}, i, j))$ is the mean absolute difference between the cardiac image $V_k(P_l, i, j)$ of the current cardiac motion phase and a cardiac image $V_k(P_{l+1}, i, j)$ of a cardiac motion phase that occurs after the current cardiac motion phase; $\Delta M(P_l, k)$ is the cardiac motion parameter corresponding to the cardiac image of the current cardiac motion phase.

In Equation (2), $P_l$ is the current cardiac motion phase, l is a sequence number of the current cardiac motion phase in the plurality of cardiac motion phases, k is a sequence number of a slice of the object, i and j represent the element locations in a corresponding cardiac image. In some embodiments, the number (or count) of the cardiac motion parameters (e.g., the $\Delta M(P_l, k)$ in Equation (2)) may be less than the number (or count) of the cardiac motion phases.

In 7406, a mean phase may be determined based on the plurality of cardiac motion parameters corresponding to the plurality of cardiac motion phases.

In some embodiments, the processing device 140 (e.g., the image selection module 13400) may perform operation 7406. In some embodiments, a first mean phase in the systolic period and/or a second mean phase in the diastolic period may be determined.

Specifically, in some embodiments, in a systolic period of cardiac motion, a cardiac motion phase corresponding to a minimum cardiac motion parameter in the systolic period may be designated as the mean phase in the systolic period. In a diastolic period of cardiac motion, a cardiac motion phase corresponding to a minimum cardiac motion parameter in the diastolic period may be designated as the mean phase in the diastolic period.

In some embodiments, the determination of the mean phase in the systolic period may be represented as:

$$P_{Basic}1 = \arg_l \min(\Sigma_k^N \Delta M(P_l, k)/N), \text{ for all } P_l \text{ where } P_{1S} \leq P_l \leq P_{1E}, \quad (3)$$

where $P_{Basic}1$ is the mean phase in the systolic period; N is the number (or count) of cardiac images of the cardiac motion phases in the systolic period; ($P_{1S} \leq P_l \leq P_{1E}$) is the range of the cardiac motion phases in the systolic period.

In Equation (3), $P_{1E}$ is the end phase in the systolic period, and $P_{1S}$ is the start phase in the systolic period.

In an embodiment, the determination of the mean phase in the diastolic period may be represented as:

$$P_{Basic}2 = \arg_l \min(\Sigma_k^N \Delta M(P_l, k)/N), \text{ for all } P_l \text{ where } P_{2S} \leq P_l \leq P_{2E}, \quad (4)$$

where $P_{Basic}2$ is the mean phase in the diastolic period; N is the number (or count) of cardiac images of the cardiac motion phases in the diastolic period; ($P_{2S} \leq P_l \leq P_{2E}$) is the range of cardiac motion phases in the diastolic period.

In Equation (4), $P_{2E}$ is the end phase in the diastolic period, $P_{2S}$ is the start phase in the diastolic period.

According to the process for determining the mean phase described above, the cardiac motion parameters of the corresponding cardiac motion phases may be determined based on the mean absolute differences between each two cardiac images of each two adjacent cardiac motion phases, and the cardiac motion phase with the minimum (or maximum) cardiac motion parameter may be designated as the mean phase. Therefore, the mean phase may be determined accurately, and the accuracy of the determination of the optimal phase in the cardiac motion may be ensured.

Figure 8:
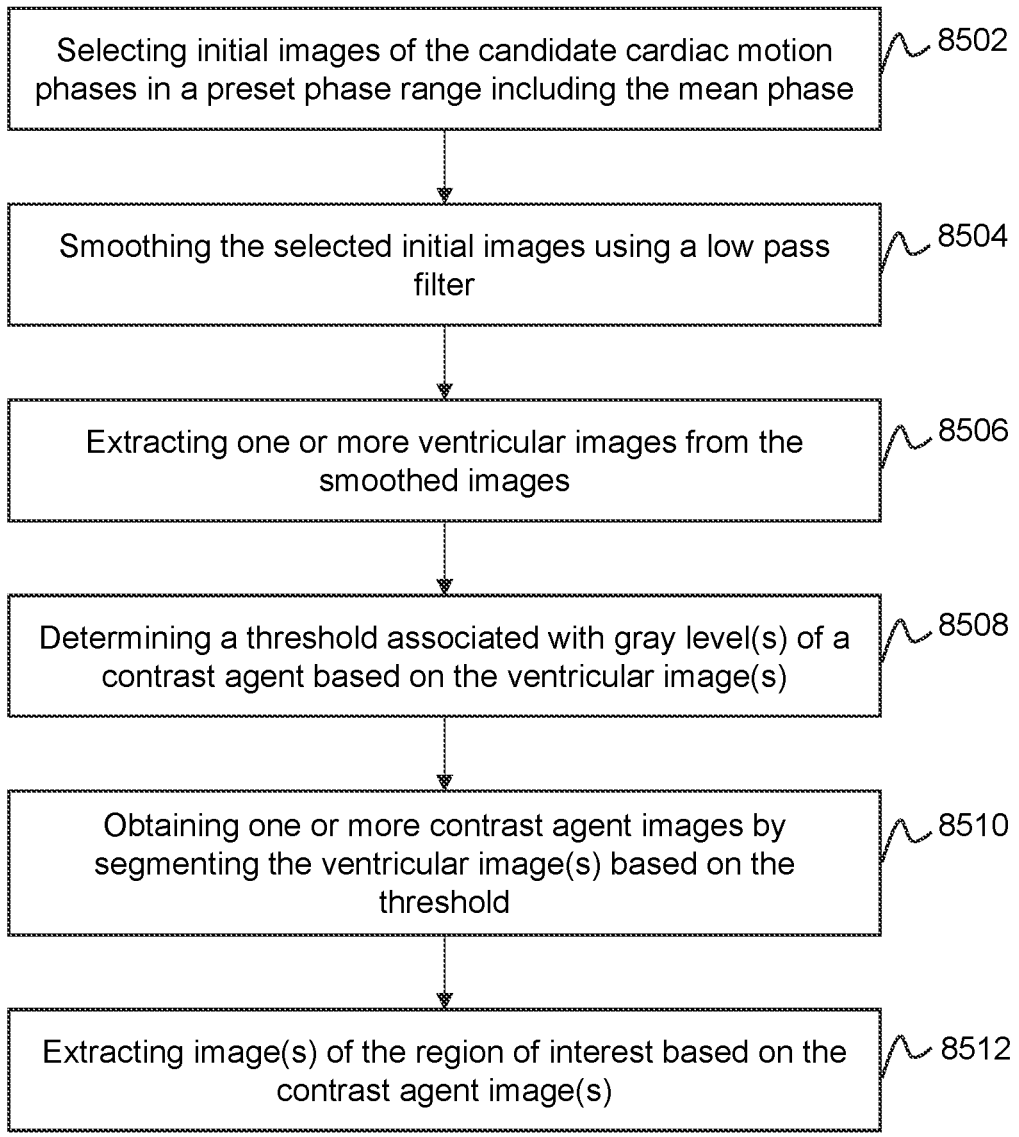
FIG. 8 is a flowchart illustrating an exemplary process for extracting an image of a region of interest according to some embodiments of the present disclosure.

FIG. 8 is a flowchart illustrating an exemplary process for extracting an image of a region of interest according to some embodiments of the present disclosure. In some embodiments, the process 800 may be executed by the imaging system 100. For example, the process 800 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, operation 6306 of FIG. 6 may be performed according to one or more operations of the process 800 in FIG. 8.

In some embodiments, as shown in FIG. 8, an exemplary process for extracting an image of a region of interest is provided. The process 800 may include one or more of the following operations:

In 8502, initial images of the candidate cardiac motion phases may be selected in a preset phase range including the mean phase.

In some embodiments, the processing device 140 (e.g., the image selection module 13400) may perform operation 8502. More descriptions of the preset phase range may be found elsewhere in the present disclosure (e.g., FIG. 5 and descriptions thereof).

Specifically, in some embodiments, the preset phase range may be centered at the mean phase, and may be obtained by extending the mean phase for a certain number of phases. If the preset phase range is too small, the phase of interest may be not included in the preset range. If the phase range is too large, the target region(s) in a series of target images of the phase of interests in different cardiac cycles may be discontinuous. Therefore, the setting of the preset range may be important. In some embodiments, the preset range may be centered at the mean phase, with 10% forward extension and 10% backward extension.

In some embodiments, a first preset range may be determined based on the first mean phase in the systolic period, and/or a second preset range may be determined based on the second mean phase in the diastolic period. The first preset range associated with the systolic period may also be referred to as a systolic preset range. The second preset range associated with the diastolic period may also be referred to as a diastolic preset range.

In 8504, the selected initial images may be smoothed using a low pass filter.

In some embodiments, the processing device 140 (e.g., the image selection module 13400) may perform operation 8504.

Specifically, in some embodiments, the selected initial images within the preset range may be smoothed using a Gaussian low-pass filter. The Gaussian low-pass filter may eliminate the effects of noise and produces smoothed images for subsequent image processing.

In 8506, one or more ventricular images may be extracted from the smoothed images.

In some embodiments, the processing device 140 (e.g., the image selection module 13400) may perform operation 8506. In some embodiments, the processing device 140 may extract a ventricular image based on each smoothed image.

Specifically, in some embodiments, image segmentation may be performed according to the smoothed image(s) and a threshold associated with bone(s). In some embodiments, elements of a smoothed image that have gray levels higher than the threshold associated with bone(s) may be extracted as a bone image. In some embodiments, one or more bone images may be obtained similarly based on the smoothed images. In some embodiments, a maximum intensity projection may be performed on the bone image(s) in an axial direction of the thoracic cavity, and a maximum intensity projection image of the bone image(s) may be obtained. The maximum intensity projection may be generated based on element(s) having a maximum intensity (or density) along each projection ray directed to the object's target site. That is, if the projection ray passes through the smoothed images, the element(s) with the highest intensity (or density) in the image(s) may be retained and projected onto a two-dimensional plane, thereby forming a maximum intensity projection image of the bone image(s). According to the maximum intensity projection image of the bone image(s), the maximum intensity projection image (e.g., elements of the maximum intensity projection image) of the bone image(s) may correspond to different Boolean values. A thoracic contour boundary may be determined according to boundaries of the different Boolean values. In some embodiments, a pleural image may be obtained based on the smoothed images and the thoracic contour boundary. In some embodiments, elements within the thoracic contour boundary may be extracted from the smoothed images to obtain a pleural image (or thoracic contour image). Then, connected domain(s) may be determined based on a pleural image; a target connected domain with a maximum number of elements among the connected domain(s) may be extracted as a ventricular image. A connected domain may correspond to a region in a complex plane. If a simple closed curve is used in the complex plane, and the internal of the closed curve always belongs to the region, then the region is a connected domain.

Figure 9:
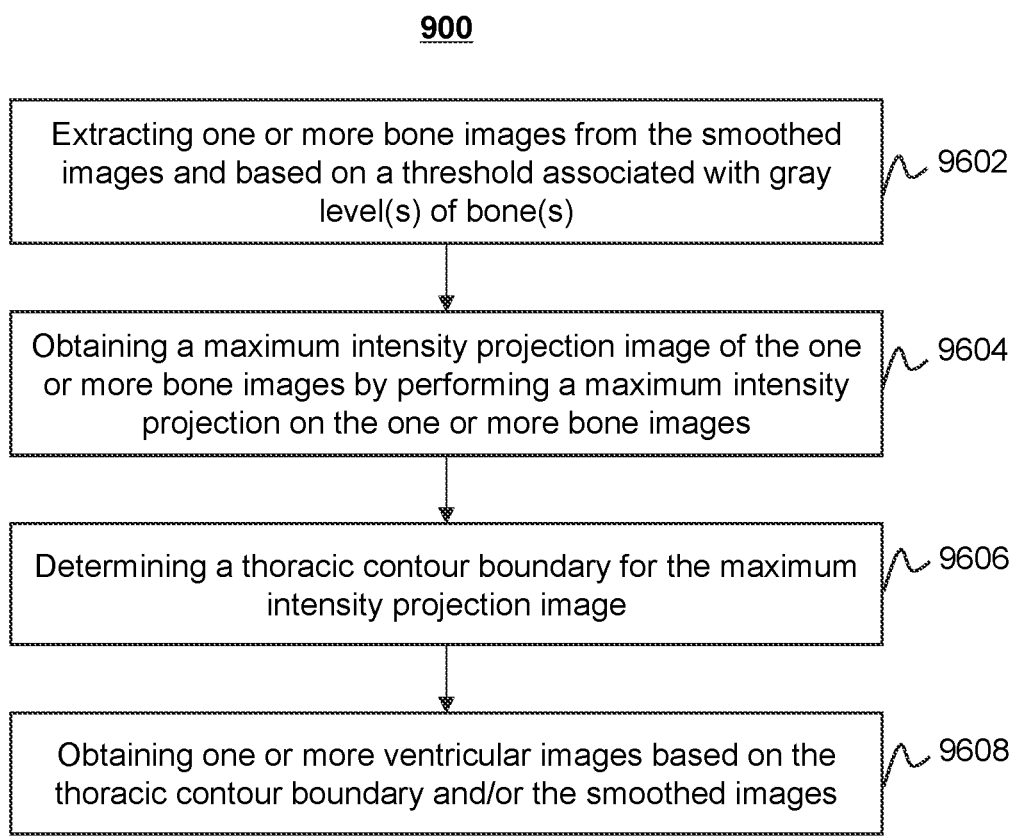
FIG. 9 is a flowchart illustrating an exemplary process for extracting a ventricular image according to some embodiments of the present disclosure.

More descriptions of the extraction of the ventricular images may be found elsewhere in the present disclosure (e.g., FIG. 9 and descriptions thereof).

In 8508, a threshold associated with gray level(s) of a contract agent may be determined based on the ventricular image(s).

In some embodiments, the processing device 140 (e.g., the image selection module 13400) may perform operation 8508.

Specifically, in some embodiments, the extraction of the image(s) of the region of interest may be performed based on image segmentation using the threshold associated with gray level(s) of the contrast agent. The CT values of different concentrations of contrast agents are different, and the segmentation of the region(s) including the contrast agent may not be performed based on an empirical threshold. Therefore, it is necessary to determine the threshold associated with the contrast agent according to the current obtained image(s). In some embodiments, gradient image(s) of the ventricular image(s) may be determined based on the ventricular image(s). In image processing, modulus (or moduli) of gradient(s) may be simply referred to as gradient(s), and an image using the gradient(s) as elements may be referred to as a gradient image. If an image (e.g., a ventricular image) includes an edge (e.g., of different portions of an object), a corresponding gradient image may include relatively large gradient value(s). If the image includes a relatively smooth part, and difference(s) between gray level(s) are relatively low, then the corresponding gradient value(s) may be relatively low. In some embodiments, the determination of the gradient image(s) may be performed using the Sobel operator. The Sobel operator is a discrete first-order difference operator used to determine an approximation of a first-order gradient of an image brightness function. A gradient vector corresponding to an element of an image may be generated by applying the Sobel operator to the element in the image. In some embodiments, the gray level(s) of the element(s) in the gradient image may be analyzed statistically, and a target ventricular image whose corresponding gradient image has elements with values larger than a proportional threshold may be determined as a marker image. In some embodiments, the gray level(s) of the element(s) in the gradient image may be analyzed statistically to obtain a histogram of the element(s); an appropriate proportion of gray level(s) may be selected as a proportional threshold; and the element(s) with gray level(s) greater than the proportional threshold may be extracted to obtain a marker image. In some embodiments, the threshold associated with the contrast agent may be determined based on the value(s) of the element(s) of the marker image using the OTSU algorithm. The OTSU algorithm is an efficient algorithm for the binarization of image(s), using a threshold to segment an original image into a foreground image and a background image. An optimal segmentation threshold may be taken as the threshold associated with the gray level(s) of the contrast agent.

In 8510, one or more contrast agent images may be obtained by segmenting the ventricular image(s) based on the threshold.

In some embodiments, the processing device 140 (e.g., the image selection module 13400) may perform operation 8510. In some embodiments, the processing device 140 may obtain a contrast agent image by segmenting each ventricular image based on the threshold.

Specifically, in some embodiments, the image segmentation may be performed based on the threshold associated with the contrast agent. Element(s) with gray level(s) greater than the threshold associated with the contrast agent may be extracted from the ventricular image(s) to obtain the contrast agent image(s).

In 8512, image(s) of the region of interest (or vascular image(s) of interest) may be extracted based on the contrast agent image(s).

In some embodiments, the processing device 140 (e.g., the image selection module 13400) may perform operation 8512.

Specifically, in some embodiments, the right coronary artery is an arterial blood vessel that is clinically more visible than other blood vessels, the motion of the right coronary artery may reflect the motion of the heart, and then the motion of the heart in different phases may be determined by detecting the motion of the right coronary artery in the corresponding phases. In some embodiments, in the contrast agent image(s), image(s) having a relatively low amount of elements associated with the contrast agent and having elements with relatively low extravascular CT values may be extracted from portion(s) of the contrast agent image(s) corresponding to the upper left half of the ventricle to obtain the vascular image(s) of interest.

According to the process for extracting the vascular image(s) of interest described above, ventricular image(s) may be extracted from the smoothed images; the threshold associated with gray level(s) of the contrast agent may be determined according to the ventricular image(s); the ventricular image(s) may be segmented based on the threshold associated with the contrast agent to obtain the contrast agent image(s); and the vascular image(s) of interest may be extracted from the contrast agent image(s). Therefore, right coronary vascular image(s) may be determined accurately in the images of the preset phase range, thereby improving the accuracy of the determination of the optimal phase (or phase of interest) in the cardiac motion.

FIG. 9 is a flowchart illustrating an exemplary process for extracting a ventricular image according to some embodiments of the present disclosure. In some embodiments, the process 900 may be executed by the imaging system 100. For example, the process 900 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 900 presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, operation 8506 of FIG. 8 may be performed according to one or more operations of the process 900 in FIG. 9.

In some embodiments, as shown in FIG. 9, an exemplary process for extracting ventricular image(s) is provided. The process 900 may include one or more of the following operations:

In 9602, one or more bone images may be extracted from the smoothed images and based on a threshold associated with gray level(s) of bone(s).

In some embodiments, the processing device 140 (e.g., the image selection module 13400) may perform operation 9602.

Specifically, in some embodiments, according to the threshold associated with the bone(s), bone image(s) that have elements with gray level(s) larger than the threshold associated with the bone(s) may be extracted. The threshold associated with the bone(s) in the thoracic cavity may generally be around 1500 HU according to the clinical experience. That is, region(s) including elements with gray level(s) greater than 1500 HU may be extracted from the smoothed images and may be regarded as the bone image(s).

In 9604, a maximum intensity projection image of the one or more bone images may be obtained by performing a maximum intensity projection on the one or more bone images.

In some embodiments, the processing device 140 (e.g., the image selection module 13400) may perform operation 9604.

Specifically, in some embodiments, the maximum intensity projection image may be generated based on element(s) having a maximum intensity (or density) along each projection ray directed to the target site of the object. That is, if the projection ray passes through the smoothed images, the element(s) with the highest intensity (or density) in the image(s) may be retained and projected onto a two-dimensional plane, thereby forming a maximum intensity projection image of the bone image(s).

In 9606, a thoracic contour boundary may be determined for the maximum intensity projection image.

In some embodiments, the processing device 140 (e.g., the image selection module 13400) may perform operation 9606.

Specifically, in some embodiments, according to the maximum intensity projection image of the bone image(s), the Boolean value of elements in a ventricular region of the maximum intensity projection image of the bone image(s) may be set as 1, and the Boolean value of elements in the non-ventricular region of the maximum intensity projection image of the bone image(s) may be set as 0. A boundary of elements with Boolean value 1 and elements with Boolean value 0 may be taken as a thoracic contour boundary.

In some embodiments, a thoracic contour boundary may correspond to a binary image, wherein elements inside the thoracic contour boundary may have the Boolean value 1, while elements outside the thoracic contour boundary may have the Boolean value 0. In some embodiments, the thoracic contour boundary may include one or more elements representing one or more positions of a thoracic contour boundary of an object.

In 9608, one or more ventricular images may be obtained based on the thoracic contour boundary and/or the smoothed images.

In some embodiments, the processing device 140 (e.g., the image selection module 13400) may perform operation 9608.

Specifically, in some embodiments, a pleural image may be obtained according to the smoothed images and the thoracic contour boundary. Connected domain(s) may be determined according to the pleural image, and a target connected domain with a maximum number of elements among the connected domain(s) may be identified as a ventricular (mask) image.

According to the smoothed images and the thoracic contour boundary, a pleural image may be obtained. A region within a thoracic contour boundary may be extracted as a pleural image in one of the smoothed images. That is, a region that has specific elements may be extracted in the smoothed images as a pleural image. The specific elements may have value(s) larger than a threshold associated with soft tissue(s) and may have a Boolean value 1.

Connected domain(s) may be determined according to the pleural image, and a target connected domain with a maximum number of elements among the connected domain(s) may be designated as a ventricular (mask) image. Based on the pleural image, the target connected domain with the maximum number of elements may be designated as the ventricular (mask) image. A connected domain may correspond to a region in a complex plane. If a simple closed curve is used in the complex plane, and the internal of the closed curve always belongs to the region, then the region is a connected domain.

In some embodiments, the ventricular image(s) may be obtained based on the ventricular mask image and the smoothed images.

According to the process for extracting the ventricular image(s), image segmentation may be performed on the smoothed image(s) based on a threshold associated with bone(s) to obtain bone image(s); a maximum intensity projection may be performed on the bone image(s) to obtain a maximum intensity projection image. The process may further include determining a thoracic contour boundary according to the maximum intensity projection image, extracting a region within the thoracic contour boundary as a pleural image, determining connected domain(s) of the pleural image, and designating a target connected domain with the maximum number of elements as the ventricular (mask) image. Therefore, the thoracic contour boundary may be accurately determined, thereby improving the accuracy of the determination of the ventricular image(s), and improving the accuracy of the determination of the heart region.

Figure 10:
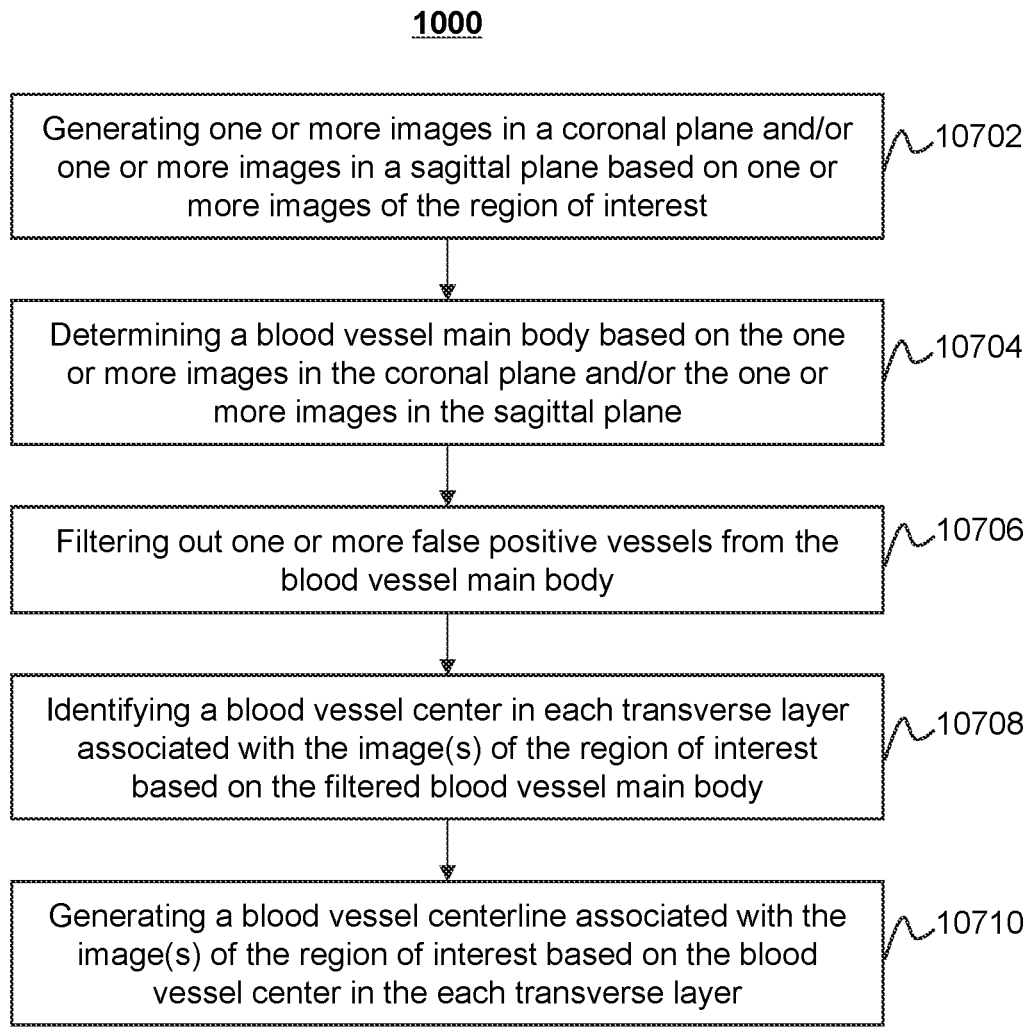
FIG. 10 is a flowchart illustrating an exemplary process for extracting a blood vessel centerline associated with image(s) of a region of interest according to some embodiments of the present disclosure.

FIG. 10 is a flowchart illustrating an exemplary process for extracting a blood vessel centerline associated with image(s) of a region of interest according to some embodiments of the present disclosure. In some embodiments, the process 1000 may be executed by the imaging system 100. For example, the process 1000 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 1000 presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. In some embodiments, operation 6308 of FIG. 6 may be performed according to one or more operations of the process 1000 in FIG. 10.

In some embodiments, as shown in FIG. 10, an exemplary process for extracting a blood vessel centerline is provided. The process 1000 may include one or more of the following operations:

In 10702, one or more images in a coronal plane and/or one or more images in a sagittal plane may be generated based on one or more images of the region of interest (e.g., the image(s) of the region of interest obtained in operation 6306 of process 600).

In some embodiments, the processing device 140 (e.g., the image selection module 13400) may perform operation 10702.

Specifically, in some embodiments, the image(s) of the region of interest (obtained in 6306) may have one or more connected domains. In some embodiments, the connected domain(s) may include a branch of a blood vessel that does exist in a current transverse layer, and/or one or more other connected domains of non-vascular regions. Exemplary connected domains of non-vascular regions like calcification, metal(s), and/or bone(s) may be classified into regions of interest. Therefore, for subsequent image processing, false positive vessel(s) may need to be excluded, and the blood vessel centerline may be extracted. In some embodiments, the blood vessels are continuous in both the coronal plane and the sagittal plane. Therefore, the image(s) in the coronal plane and image(s) in the sagittal plane may be generated first to further filter out false positive vessel(s). The image(s) in the coronal plane and image(s) in the sagittal plane may be obtained based on the image(s) of the region of interest. The coronal plane may also be referred to as the frontal plane, that is, along the left and right direction of the object and along the longitude axis of the object, the object may be longitudinally segmented into the anterior and posterior sections. The sagittal plane may be an anatomical plane that segments the object into left and right sections.

In some embodiments, each image of the region of interest may be an image in a transverse plane. In some embodiments, volume data (corresponding to a plurality of voxels) may be generated based on the images of the region of interest. In some embodiments, the volume data may be generated by performing a three-dimensional reconstruction technique based on the images of the region of interest, and accordingly, the image(s) in the coronal plane and the image(s) in the sagittal plane may be obtained based on the volume data. The three-dimensional reconstruction technique may include multiplanar reconstruction (MPR). The MPR may stack a plurality of axial images (e.g., traverse images) within the scanning scope, and then perform image reformation on a specified tissue or in a specified scope in the coronal plane, the sagittal plane or an oblique plane with any angle, so that a new slice image in coronal plane, sagittal plane or oblique plane with any angle may be generated.

Alternatively, the image(s) of the region of interest may be image(s) in the coronal plane (or the sagittal plane), and the images in other planes (e.g., the sagittal plane, the transverse plane, or the like) may be generated according to the three-dimensional reconstruction technique (e.g., MPR) similarly.

In 10704, a blood vessel main body may be determined based on the one or more images in the coronal plane and/or the one or more images in the sagittal plane.

In some embodiments, the processing device 140 (e.g., the image selection module 13400) may perform operation 10704.

Specifically, in some embodiments, the blood vessel main body may be located in the middle part of the image(s) of the region of interest (or the volume data) and/or in the largest connected domain of the image(s) of the region of interest (or the volume data). In some embodiments, the blood vessel main body may be determined based on the image(s) in the coronal plane and/or the image(s) in the sagittal plane.

In 10706, one or more false positive vessels may be filtered out from the blood vessel main body.

In some embodiments, the processing device 140 (e.g., the image selection module 13400) may perform operation 10706.

Specifically, in some embodiments, according to the blood vessel main body (also referred to as a main blood vessel), the non-main blood vessels may be filtered out, and the main blood vessel(s) may be further filtered according to the blood vessel main body after filtering the non-main blood vessels. False positive vessels may include or refer to non-vascular regions. In some embodiments, a true positive blood vessel may satisfy one or more criteria. A first criterion may relate to smoothness, which means the distance between a candidate blood vessel (or a blood vessel to be determined) and the already determined vessel in the X axis direction may not be too large, and/or the distance between the candidate blood vessel and the determined blood vessel in the transverse plane may not be too large. The position of the candidate blood vessel may refer to the position of the maximum value of the connected domain of the non-main region. The position of the determined blood vessel may refer to the maximum value of the main blood vessel closest to the candidate blood vessel. A second criterion may relate to continuity, which means the distance of the candidate blood vessel and the determined blood vessel in the Y axis direction (or the Z axis direction) may not be too large (e.g., may be no large than a threshold). In some embodiments, the distance of the candidate blood vessel and the determined blood vessel in the axial direction of the determined blood vessel may not be too large (e.g., may be no large than a threshold). In some embodiments, the distance of the candidate blood vessel and the determined blood vessel in the radial direction of the determined blood vessel may not be too large (e.g., may be no large than a threshold). If a connected domain is not detected in a transverse layer, the distance may increase by 1. If a connected domain is not detected in a plurality of transverse layers (e.g., the distance exceeds a threshold), it may be determined that the continuity criterion is not satisfied. In some embodiments, if the candidate blood vessel satisfies the smoothness criterion and continuity criterion simultaneously, the candidate blood vessel may be determined as a determined blood vessel. In some embodiments, the mean value of the positions of all the determined blood vessels in the X axis direction may be determined. In some embodiments, the candidate blood vessel closest to the mean value may be determined as an effective blood vessel. In some embodiments, the mean value of the positions of all the determined blood vessels among the main blood vessels in the X axis direction may be determined. In some embodiments, the candidate blood vessel closest to the mean value may be determined as an effective blood vessel.

In some embodiments, after filtering the non-main blood vessels, the main blood vessel(s) may be further filtered to identify an effective blood vessel among one or more main blood vessels. In some embodiments, for the blood vessels near the two ends of the blood vessel main body, the mean value of the positions of all the determined blood vessels in the X axis direction may be determined, and the candidate blood vessel closest to the mean value may be determined as an effective blood vessel. In some embodiments, for the blood vessels near a middle segment of the blood vessel main body, the mean value of the positions of all the determined blood vessels among the main blood vessels in the X axis direction may be determined, and the candidate blood vessel closest to the mean value may be determined as an effective blood vessel.

In 10708, a blood vessel center may be identified in each transverse layer associated with the image(s) of the region of interest based on the filtered blood vessel main body.

In some embodiments, the processing device 140 (e.g., the image selection module 13400) may perform operation 10708.

Specifically, in some embodiments, the blood vessel centers may be determined using interpolation according to the main blood vessel obtained after filtering out the false positive vessels. In some embodiments, the position of the blood vessel center in each transverse layer may be determined according to the positions of the blood vessel centers in the sagittal plane and the coronal plane.

In 10710, a blood vessel centerline associated with the image(s) of the region of interest may be generated based on the blood vessel center in the each transverse layer.

In some embodiments, the processing device 140 (e.g., the image selection module 13400) may perform operation 10710.

According to the process for extracting the blood vessel centerline corresponding to the image(s) of the region of interest, image(s) in a coronal plane and/or image(s) in a sagittal plane may be generated based on the image(s) of the region of interest; a blood vessel main body may be determined; one or more false positive vessels may be filtered out from the blood vessel main body; a blood vessel center may be identified in each transverse layer associated with the image(s) of the region of interest; a blood vessel centerline associated with the image(s) of the region of interest may be generated. Therefore, the image(s) of the region of interest may be accurately determined, thereby improving the accuracy of the determination of the heart region.

FIG. 11 is a flowchart illustrating an exemplary process for determining image(s) to be evaluated according to some embodiments of the present disclosure. In some embodiments, the process 1100 may be executed by the imaging system 100. For example, the process 1100 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 1100 presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting. In some embodiments, operation 6310 of FIG. 6 may be performed according to one or more operations of the process 1100 in FIG. 11.

In some embodiments, as shown in FIG. 11, an exemplary process for determining image(s) to be evaluated is provided. The process 1100 may include one or more of the following operations:

In 11802, a transformed image of the region of interest may be generated by performing a top-hat transformation on each image of the region of interest.

In some embodiments, the processing device 140 (e.g., the image selection module 13400) may perform operation 11802.

Specifically, the top-hat transformation is an image processing algorithm that may weaken a background in an image and make a target object more prominent. That is, the top-hat transformation of the image of the region of interest may make a target region in the image of the region of interest more prominent. In some embodiments, the target object may include a blood vessel. In some embodiments, after the top-hat transformation of the image of the region of interest, the background (in the image of the region of interest) may be weakened and the blood vessel(s) (in the image of the region of interest) may be shown more clearly.

In 11804, an image including the intraventricular region may be generated by segmenting, based on a threshold associated with gray level(s) of soft tissue(s), the transformed image of the region of interest.

In some embodiments, the processing device 140 (e.g., the image selection module 13400) may perform operation 11804.

Specifically, in some embodiments, an empirical threshold associated with the gray level(s) of the soft tissue(s) may be 800 HU. According to the threshold associated with the gray level(s) of soft tissue(s), the transformed image of region of interest may be segmented to obtain an image that reserves the intraventricular region. The image that reserves the intraventricular region may be also referred to as an image including the intraventricular region.

In 11806, an image to be evaluated may be obtained by extracting, based on a preset region including the blood vessel centerline, elements of the image including the intraventricular region.

In some embodiments, the processing device 140 (e.g., the image selection module 13400) may perform operation 11806.

Specifically, in some embodiments, an image (to be evaluated) of a corresponding cardiac motion phase may be obtained by extracting, based on a preset region including the blood vessel centerline, elements of the image including the intraventricular region. In some embodiments, each transverse layer may have a corresponding preset region. In some embodiments, a preset region of a transverse layer may be centered at a blood vessel center in the transverse layer and may have a size of N*N. In some embodiments, the pixels in the preset region may be extracted as the image to be evaluated in the transverse layer. In some embodiments, N may refer to a physical size within 50-100 mm. In some embodiments, before segmentation, it may be necessary to determine whether N exceeds the boundary of the current image including the intraventricular region. If N exceeds the boundary of the current image, it may be necessary to pad the image before segmentation. The padded value may be 0 or the value(s) of the element(s) of the boundary. In some embodiments, the images to be evaluated may be extracted from the images of phases within the preset range (e.g., 10%) around the mean phase, and the image matrixes to be evaluated in the systolic preset range and/or the image matrixes to be evaluated in the diastolic preset range may be obtained.

According to the process for extracting the images to be evaluated, the range of the images to be evaluated may be determined accurately according to the blood vessel centerline, and thereby improving the accuracy of the determination of the phase of interest.

Figure 12:
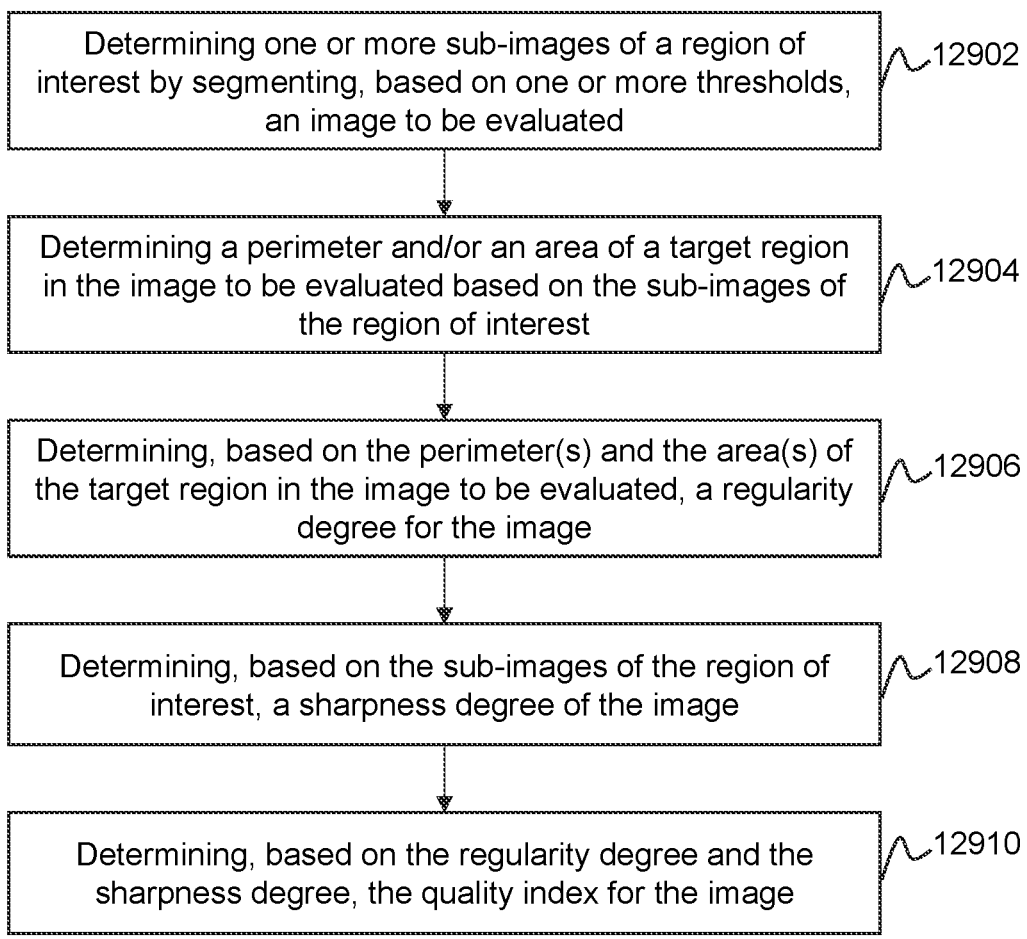
FIG. 12 is a flowchart illustrating an exemplary process for determining a quality index of an image to be evaluated according to some embodiments of the present disclosure.

FIG. 12 is a flowchart illustrating an exemplary process for determining a quality index of an image to be evaluated according to some embodiments of the present disclosure. In some embodiments, the process 1200 may be executed by the imaging system 100. For example, the process 1200 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 1200 presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting. In some embodiments, operation 5204 of FIG. 5 may be performed according to one or more operations of the process 1200 in FIG. 12.

In 12902, one or more sub-images of a region of interest may be determined by segmenting, based on one or more thresholds, an image to be evaluated.

In some embodiments, the processing device 140 (e.g., the quality index determination module 13500) may perform operation 12902. In some embodiments, operation 12902 may be similar to operation 4104. The image to be evaluated in 12902 may be an image obtained in 4102, an image obtained in 11806, etc. In some embodiments, the region of interest may include blood vessel(s). In some embodiments, each sub-image of the region of interest may refer to a vascular image of interest.

Specifically, in some embodiments, before determining the quality index, the resolution of the image to be evaluated may be improved. Improvement of the resolution(s) may cause the improvement of the accuracy of determination of the blood vessel morphologies and/or the blood vessel boundaries. In some embodiments, the resolution(s) of the image(s) may be improved using a two-dimensional image interpolation algorithm. In some embodiments, the maximum gray level of the image to be evaluated may be selected. In some embodiments, the maximum gray level multiplied by one or more predetermined multiples may be designated as one or more thresholds for segmenting the images to be evaluated. In some embodiments, elements of the image (to be evaluated) with gray level(s) larger than (and/or equal to) a segmentation threshold may be extracted as a vascular image of interest corresponding to the segmentation threshold. In some embodiments, two or more vascular images of interest may be obtained by segmenting the image based on two or more segmentation thresholds. For example, three segmentation thresholds may be obtained according to the maximum gray level of the image multiplied by three predetermined multiples. In some embodiments, the image may be segmented based on a first segmentation threshold of the three segmentation thresholds. For example, a region of the image having elements with gray levels of greater than the first segmentation threshold may be designated as a first vascular image of interest. In some embodiments, the image may be segmented based on a second segmentation threshold of the three segmentation thresholds. For example, a region of the image having elements with gray levels greater than the second segmentation threshold may be designated as a second vascular image of interest. In some embodiments, the image may be segmented based on a third segmentation threshold of the three segmentation thresholds. For example, a region of the image having elements with gray levels greater than the third segmentation threshold may be designated as a third vascular image of interest.

In 12904, a perimeter and/or an area of a target region in the image to be evaluated may be determined based on the sub-images of the region of interest.

In some embodiments, the processing device 140 (e.g., the quality index determination module 13500) may perform operation 12904. In some embodiments, the target region in the image may also be referred to as the region of interest in the image, for example, a region of a blood vessel.

Specifically, in some embodiments, the perimeter and/or the area of the target region in the image to be evaluated may be determined according to the sub-images of the region of interest (or vascular images of interest). That is, the perimeter and the area of the blood vessel in each vascular image of interest may be respectively determined. Therefore, one or more perimeters and/or one or more areas of the target regions in the sub-images of the region of interest may be determined.

In some embodiments, connected domains of the sub-images of the region of interest may be obtained. In some embodiments, if the number (or count) of the elements in a connected domain is no less than a first threshold, and/or the contrast of the elements in the connected domain is no less than a second threshold, then the connected domain may be determined as a target region to be evaluated. Accordingly, the perimeter and/or the area of the target region (e.g., the qualified or identified connected domains) may be determined.

In 12906, a regularity degree for the image to be evaluated may be determined based on the perimeter(s) and the area(s) of the target region in the image.

In some embodiments, the processing device 140 (e.g., the quality index determination module 13500) may perform operation 12906. More descriptions of the determination of the regularity degree may be found in Chinese Patent Application No. 201811133622.6 entitled "METHODS, SYSTEMS, COMPUTING DEVICES, AND READABLE STORAGE MEDIA FOR CARDIAC IMAGE RECONSTRUCTION," filed on Sep. 27, 2018, and Chinese Patent Application No. 201811133609.0 entitled "METHODS, SYSTEMS, COMPUTING DEVICES, AND READABLE STORAGE MEDIA FOR CARDIAC IMAGE RECONSTRUCTION," filed on Sep. 27, 2018, and U.S. application Ser. No. 16/437,003, entitled "SYSTEMS AND METHODS FOR RECONSTRUCTING CARDIAC IMAGES," filed on even date, the contents of which are hereby incorporated by reference. For example, the regularity degree may be determined based on a compactness degree. In some embodiments, the compactness degree may reflect a closeness degree of the element(s) in an image or a region of interest thereof. The compactness degree may relate to a perimeter and/or an area of a region (e.g., the target object) including a portion or all elements in the image or a region of interest thereof. In some embodiments, the compactness degree may be in direct proportion to the perimeter and/or inversely proportional to the area.

In 12908, a sharpness degree of the image may be determined based on the sub-images of the region of interest.

In some embodiments, the processing device 140 (e.g., the quality index determination module 13500) may perform operation 12908. In some embodiments, the sharpness degree of the image may be determined according to the edge(s) of the vascular image(s) of interest, and/or the gradient map(s) of the vascular image(s) of interest. In some embodiments, the sharpness degree of an image may be determined based on a cross product of the edge of the image and the gradient map of the image.

In some embodiments, the processing device 140 may identify connected domain(s) in the sub-image(s) of the image to be evaluated. In some embodiments, the target object in the image to be evaluated may refer to the identified connected domain(s) in the sub-image(s) of the image. In some embodiments, for each of the identified connected domains in the image, the processing device 140 may determine an edge of the identified connected domain, and/or determine a gradient map of the identified connected domain. Therefore, one or more edges and/or one or more gradient maps may be determined for the image to be evaluated. Further, the processing device 140 may determine, based on the one or more edges and/or the one or more gradient maps, the sharpness degree of the image. In some embodiments, the processing device 140 may determine the number (or count) of the identified connected domain(s) in the image to be evaluated. In some embodiments, in response to a determination that the count of the identified connected domain(s) in the image is zero, the processing device 140 may designate the regularity degree of the image as zero, and/or designate the sharpness degree of the image as zero. In some embodiments, the processing device 140 may adjust, based on the count of the connected domain(s) in the image, the regularity degree for the image. In some embodiments, the processing device 140 may adjust, based on the count of the connected domain(s) in the image, the sharpness degree of the region of interest in the image.

In 12910, the quality index for the image may be determined based on the regularity degree and the sharpness degree of the image.

In some embodiments, the processing device 140 (e.g., the quality index determination module 13500) may perform operation 12910. In some embodiments, the processing device 140 may designate a weighted sum of the regularity degree and the sharpness degree as the quality index for the image. In some embodiments, the quality index for each of the images to be evaluated obtained in 4102 or 11806 may be determined similarly as illustrated above.

In some embodiments, the number (or count) of target regions (e.g., blood vessels) in different images may be inconsistent if the images are detected based on a same target object (e.g., at an identical physical position) but at different cardiac motion phases. In some embodiments, the image quality evaluation may need to be performed on the images (e.g., the images obtained in 4102 or 11806) based on a same reference (or criteria), that is, the number (or count) of target regions (e.g., blood vessels) in the images that are detected based on a same target object (e.g., the blood vessels) at an identical physical position may need to be consistent. In some embodiments, a reference parameter (e.g., the number (or count) of basic blood vessels, or the number (or count) of blood vessels of a predetermined basic cardiac motion phase) may be introduced.

In some embodiments, according to the number (or count) of basic blood vessels and/or the number (or count) of blood vessels in each of the images to be evaluated, a regularity degree matrix of the images (to be evaluated) of each cardiac motion phase and a sharpness degree matrix of the images (to be evaluated) of each cardiac motion phase may be obtained.

An element of the regularity degree matrix may represent a regularity degree of a layer image of a cardiac motion phase. An element of the sharpness degree matrix may represent a sharpness degree of a layer image of a cardiac motion phase. In some embodiments, the number (or count) of blood vessels in each of the images to be evaluated may be compared with the number (or count) of basic blood vessels, and accordingly, the determination of the regularity degree matrix and/or the sharpness degree matrix may be adjusted based on the comparison result. For example, if the count of blood vessels in an image is equal to the count of basic blood vessels, and is larger than 1, the regularity degree of the image may be determined based on an average compactness degree of the blood vessels. As another example, if the count of blood vessels in an image is larger than 1 and the count of basic blood vessels, and the count of basic blood vessels is larger than 0, then a same number of blood vessels as the count of basic blood vessels may be selected for the determination of the regularity degree and/or the sharpness degree. As a further example, if the count of the basic blood vessels is 0, and the count of the blood vessels in the image is larger than 1, a blood vessel nearest to a center of the image may be selected for the determination of the regularity degree and/or the sharpness degree.

In some embodiments, the magnitudes of the regularity degree(s) and the sharpness degree(s) may be different. Therefore, it is desirable to adjust the regularity degree(s) and the sharpness degree(s) to a same baseline. In some embodiments, the regularity degree(s) and/or the sharpness degree(s) may be adjusted based on a weighting process, a normalization process, or the like, or a combination thereof. In some embodiments, a quality index matrix for the diastolic period and a quality index matrix for the systolic period may be generated. In some embodiments, a quality index matrix for a specific cardiac cycle may be determined. If the number (or count) of the quality indexes with non-zero values in the quality index matrix is no less than an average number (or count) (e.g., the total number (or count) of the quality indexes with non-zero values in a plurality of cardiac cycles divided by the number (or count) of the plurality of cardiac cycles), the quality indexes of one or more images corresponding to each phase in the specific cardiac cycle may be averaged to obtain an average value, and a phase corresponding to the maximum average value may be designated as the phase of interest in the specific cardiac cycle. In some embodiments, if a cardiac cycle has no quality index matrix (e.g., all the quality indexes in the quality index matrix corresponding to the cardiac cycle are 0), the phase of interest in the cardiac cycle may be determined as equal to the phase of interest in an adjacent cardiac cycle of the current cardiac cycle. In some embodiments, a series of target images may be determined based on the phases of interest of the plurality of cardiac cycles. In some embodiments, the target image(s) of the phase of interest in a cardiac cycle may be extracted from the reconstructed images. In some embodiments, the target image(s) may be directly obtained by reconstructing the target image(s) of the phase of interest.

In some embodiments, each quality index matrix may correspond to a cardiac cycle. A quality index matrix may have a size of [K, Q], in which K refers to the number (or count) of layers for cardiac reconstruction, Q refers to the number (or count) of the plurality of cardiac motion phases. In some embodiments, in each cardiac cycle, the number (or count) of the quality indexes with non-zero values may be determined. In some embodiments, an average number (or count) may be determined based on the total number (or count) of the quality indexes with non-zero values in a plurality of cardiac cycles divided by the number (or count) of the plurality of cardiac cycles. In some embodiments, for a specific cardiac cycle, if the number (or count) of the quality indexes with non-zero values is no less than the average number (or count), then the phase of interest of the specific cardiac cycle may be determined as:

$$P_c = \arg_p(\max(\text{average}(\text{QuaIdx}_c^p))), \quad (5)$$

where c refers to the sequence number of the specific cardiac cycle in the plurality of cardiac cycles, $P_c$ refers to the phase of interest in the cth cardiac cycle, p refers to the cardiac motion phases in a cardiac cycle (e.g., the cth cardiac cycle), QuaIdx refers to a quality index matrix, and average($\text{QuaIdx}_c^p$) refers to the average value of the quality indexes of the images corresponding to the K layers of the phase p in the cth cardiac cycle.

According to the process for determining the quality index as disclosed herein, the quality index of the image may be determined more accurately, thereby improving the accuracy of the determination of the phase of interest of cardiac motion, and facilitating the determination of the target image(s) of the phase of interest.

The operations illustrated above does not rely on user interface interaction, and can automatically detect and extract the images to be evaluated, and automatically analyze the image quality of the images (e.g., vascular images). In coronary angiography, the process can be performed to automatically select the phase of interest. Users (e.g., doctors) are not required to evaluate image(s) and choose one or more phases of interest for image reconstruction. Therefore, the coronary reconstruction process may be simplified, and the users' time to evaluate image(s) and/or select parameters (e.g., the phase of interest) may be saved.

It should be understood that although the various operations in the processes of FIGS. 4-12 are displayed successfully as indicated by the arrows; these operations are not necessarily performed in the order indicated by the arrows. Except as explicitly stated herein, there is no strict ordering of the execution of these operations, and these operations can be performed in other orders. Moreover, at least a portion of the operations in FIGS. 4-12 may include a plurality of sub-steps or a plurality of stages. These sub-steps or stages are not necessarily executed at the same time, but may be executed at different times. The execution order of these sub-steps or stages is also not necessarily successful, but may be performed alternately with other operations or at least a portion of the sub-steps or stages of the other operations.

Figure 13A:
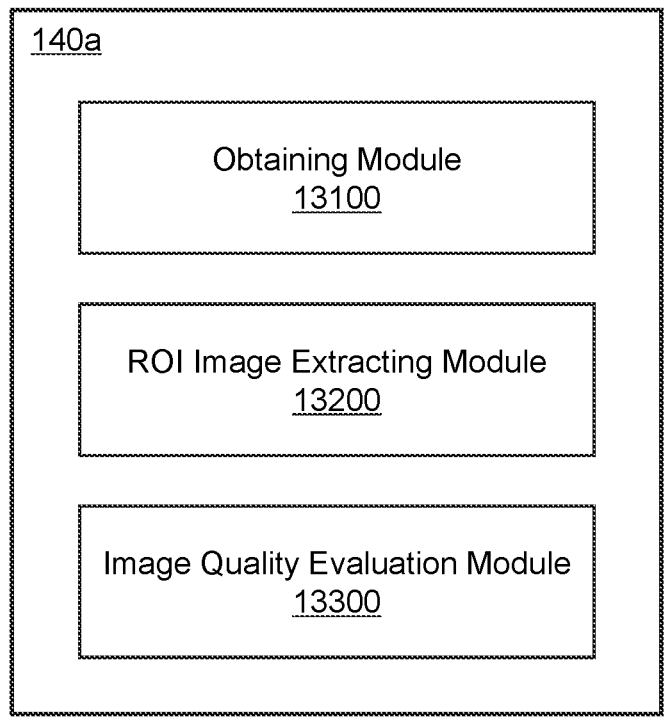
FIG. 13A is a block diagram illustrating an exemplary processing device according to some embodiments of the present disclosure.

FIG. 13A is a block diagram illustrating an exemplary processing device according to some embodiments of the present disclosure. The processing device 140a may include an obtaining module 13100, an image of region of interest extraction module (or ROI image extracting module) 13200, and an image quality evaluation module 13300. In some embodiments, the processing device 140a may also be referred to as an image quality evaluation device.

The obtaining module 13100 may be configured to obtain one or more images to be evaluated. The ROI image extracting module 13200 may be configured to obtain one or more vascular images of interest according to the image(s) to be evaluated and/or one or more segmentation thresholds. The image quality evaluation module 13300 may be configured to perform image quality evaluation according to the vascular images of interest.

More descriptions of the obtaining module 13100 may be found elsewhere in the present disclosure (e.g., FIG. 4 and descriptions thereof). More descriptions of the ROI image extracting 13200 may be found elsewhere in the present disclosure (e.g., FIG. 4 and descriptions thereof). More descriptions of the image quality evaluation module 13300 may be found elsewhere in the present disclosure (e.g., FIG. 4 and descriptions thereof).

For the specific descriptions of the image quality evaluation device, reference may be made to the descriptions of the image quality evaluation process(es) illustrated above, and details will not be repeated herein. Each module in the image quality evaluation device may be implemented in whole or in part of software, hardware, and combinations thereof. The modules can be embedded in the hardware in the processor in the computing device, or may be stored in the memory of the computing device in the form of software, so that the processor can execute the operations corresponding to the above modules.

Figure 13B:
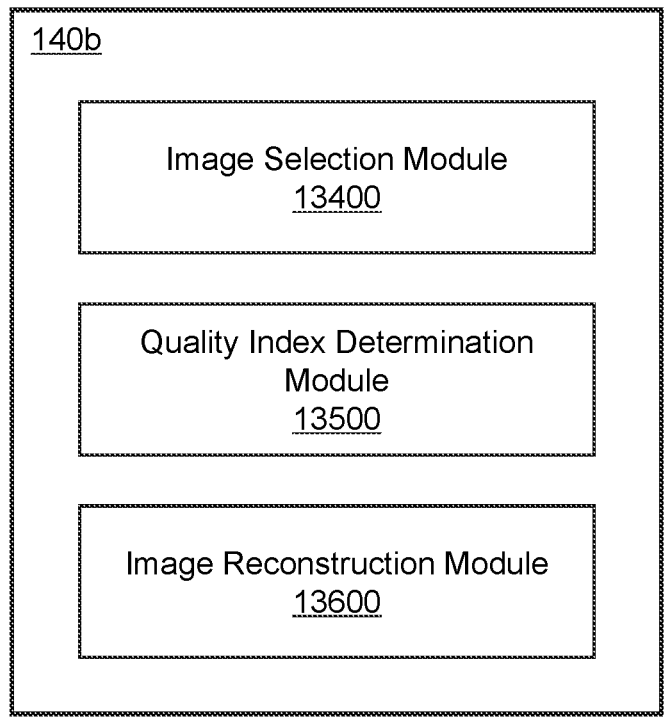
FIG. 13B is a block diagram illustrating another exemplary processing device according to some embodiments of the present disclosure.

FIG. 13B is a block diagram illustrating another exemplary processing device according to some embodiments of the present disclosure. The processing device 140b may include an image selection module 13400, a quality index determination module 13500, and an image reconstruction module 13600. In some embodiments, the processing device 140b may also be referred to as an image reconstruction device.

The image selection module 13400 may be configured to obtain projection data of a plurality of cardiac motion phases, reconstruct corresponding images of the cardiac motion phases, and/or use the reconstructed images as images to be evaluated. The quality index determination module 13500 may be configured to determine a quality index for each image to be evaluated, based on one or more image quality evaluation rules. The image reconstruction module 13600 may be configured to determine a phase of interest (in a cardiac cycle) based on the quality indexes of the images to be evaluated, and determine one or more target images of the phase of interest.

In some embodiments, the image selection module 13400 may include: a mean phase determination unit, an image of region of interest extraction unit, a blood vessel centerline extraction unit, and an image extraction unit. The mean phase determination unit may be configured to determine a mean phase based on the images of the plurality of cardiac motion phases. The image of region of interest extraction unit may be configured to select one or more candidate cardiac motion phases in a preset phase range including the mean phase; and/or obtain an image of a region of interest by extracting the region of interest in each initial image of the preset range. The blood vessel centerline extraction unit may be configured to identify a blood vessel centerline associated with the image(s) of the region of interest. The image extraction unit may be configured to obtain the images to be evaluated by segmenting, based on a preset region including the blood vessel centerline, the image(s) of the region of interest.

More descriptions of the image selection module 13400 may be found elsewhere in the present disclosure (e.g., FIGS. 5-11 and descriptions thereof). More descriptions of the quality index determination module 13500 may be found elsewhere in the present disclosure (e.g., FIGS. 5-6 and 12, and descriptions thereof). More descriptions of the image reconstruction module 13600 may be found elsewhere in the present disclosure (e.g., FIGS. 5-6 and descriptions thereof).

For the specific descriptions of the image reconstruction device, reference may be made to the descriptions of the image reconstruction process(es) illustrated above, and details will not be repeated herein. Each module in the image reconstruction device may be implemented in whole or in part of software, hardware, and combinations thereof. The modules can be embedded in the hardware in the processor in the computing device, or may be stored in the memory of the computing device in the form of software, so that the processor can execute the operations corresponding to the above modules.

It should be noted that the above description of the processing device is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140a and the processing device 140b may be integrated into a single device.

Figure 14:
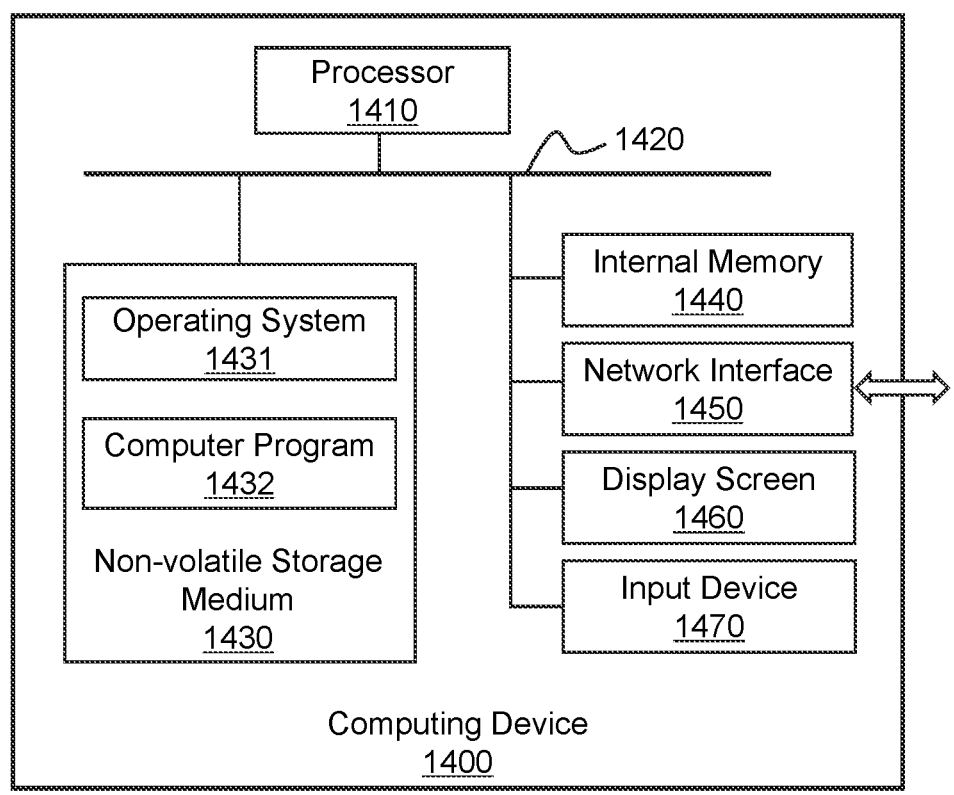
FIG. 14 is a block diagram illustrating an exemplary computing device according to some embodiments of the present disclosure.

FIG. 14 is a block diagram illustrating an exemplary computing device according to some embodiments of the present disclosure.

As shown in FIG. 14, a computing device 1400 is provided. The computing device 1400 may be a terminal. The internal components of the computing device 1400 may be shown in FIG. 14. The computing device 1400 may include a processor 1410, a memory, a network interface 1450, a display screen 1460, and an input device 1470 connected by a system bus 1420. The processor 1410 of the computing device 1400 may provide computing and/or control capabilities. The memory of the computing device 1400 may include a non-volatile storage medium 1430, an internal memory 1440. The non-volatile storage medium 1430 may store an operating system 1431 and computer program(s) 1432. The internal memory 1440 may provide an environment for operation of the operating system 1431 and the computer program(s) 1432 in the non-volatile storage medium 1430. The network interface 1450 of the computing device 1400 may communicate with an external terminal via a network connection. The computer program(s) 1432 may be executed by the processor 1410 to implement an image reconstruction process. The display screen 1460 of the computing device 1400 may include a liquid crystal display or an electronic ink display screen, and the input device 1470 of the computing device 1400 may include a touch layer covered on the display screen, or may include a button, a trajectory ball or a touchpad provided on the casing of the computing device. It may also be an external keyboard, trackpad, or mouse, or the like.

It will be understood by those skilled in the art that the structure shown in FIG. 14 is only a block diagram of a part of the structure related to the present disclosure, and does not constitute a limitation on the computing device on which the present disclosure scheme is applied. The computing device may include more or fewer components than those shown in the figures, or some components may be combined, or have different component arrangements.

In some embodiments, a computer apparatus is provided comprising a memory and a processor having computer program(s) stored therein. The processor may implement one or more of the operations illustrated above (e.g., in FIGS. 4-12) when executing the computer program(s).

In some embodiments, a non-transitory computer readable medium storing instructions is provided. The instructions, when executed by the processing device, may cause the processing device to implement one or more operations illustrated above (e.g., in FIGS. 4-12).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and at least one storage device for reconstructing a target cardiac image, the method comprising:
   determining a quality index for each cardiac image of a plurality of cardiac images corresponding to one or more cardiac motion phases of a cardiac cycle;
   determining a phase of interest for the cardiac cycle based on the plurality of quality indexes; and
   obtaining the target cardiac image of the phase of interest.

2. The method of claim 1, wherein the plurality of cardiac images corresponding to the one or more cardiac motion phases are obtained by:
   reconstructing a plurality of initial cardiac images based on projection data, the plurality of initial cardiac images corresponding to a plurality of cardiac motion phases;
   determining a mean phase based on the plurality of initial cardiac images;
   selecting one or more candidate cardiac motion phases in a preset phase range, the preset phase range including the mean phase;
   obtaining an image of a region of interest by extracting the region of interest in each initial cardiac image of one or more initial cardiac images of the one or more candidate cardiac motion phases;
   identifying a blood vessel centerline associated with the one or more images of the region of interest; and
   obtaining the each cardiac image of the plurality of cardiac images by segmenting, based on a preset region including the blood vessel centerline, each image of the region of interest.

3. The method of claim 2, wherein the determining a mean phase based on the plurality of initial cardiac images comprises:
   determining a cardiac motion parameter corresponding to each cardiac motion phase of the plurality of cardiac motion phases based on each initial cardiac image of the plurality of initial cardiac images, the cardiac motion parameter being associated with a cardiac motion rate or intensity; and
   determining the mean phase based on the plurality of cardiac motion parameters corresponding to the plurality of cardiac motion phases.

4. The method of claim 2, wherein the determining a mean phase based on the plurality of initial cardiac images comprises:
   obtaining a plurality of mean absolute differences (MADs) by determining an MAD between two initial cardiac images of each two adjacent cardiac motion phases of the plurality of cardiac motion phases;
   determining a plurality of cardiac motion parameters corresponding to the plurality of cardiac motion phases based on the plurality of mean absolute differences; and
   determining the mean phase based on the plurality of cardiac motion parameters corresponding to the plurality of cardiac motion phases.

5. The method of claim 4, wherein the determining a plurality of cardiac motion parameters corresponding to the plurality of cardiac motion phases comprises:
   determining a first mean absolute difference (MAD) between a first initial cardiac image of a first cardiac motion phase that occurs before each cardiac motion phase of the plurality of cardiac motion phases and an initial cardiac image of the each cardiac motion phase;
   determining a second mean absolute difference (MAD) between a second initial cardiac image of a second cardiac motion phase that occurs after the each cardiac motion phase and an initial cardiac images of the each cardiac motion phase; and
   designating a sum of the first mean absolute difference (MAD) and the second mean absolute difference (MAD) as the cardiac motion parameter corresponding to the each cardiac motion phase.

6. The method of claim 5, wherein the first cardiac motion phase is adjacent to the each cardiac motion phase, and the second cardiac motion phase is adjacent to the each cardiac motion phase.

7. The method of claim 4, wherein the determining the mean phase comprises:
   designating a cardiac motion phase corresponding to a minimum cardiac motion parameter in a systolic period as the mean phase in the systolic period.

8. The method of claim 4, wherein the determining the mean phase comprises:
   designating a cardiac motion phase corresponding to a minimum cardiac motion parameter in a diastolic period as the mean phase in the diastolic period.

9. The method of claim 2, wherein the obtaining an image of a region of interest by extracting the region of interest in each initial cardiac image of one or more initial cardiac images of the one or more candidate cardiac motion phases comprises:
   extracting a ventricular image from the each initial cardiac image of the one or more initial cardiac images;
   obtaining, based on the ventricular image, a first threshold associated with gray levels of a contrast agent in the one or more initial cardiac images;
   obtaining a contrast agent image by segmenting the ventricular image based on the first threshold; and
   extracting the image of the region of interest from the contrast agent image.

10. The method of claim 9, wherein the obtaining an image of a region of interest by extracting the region of interest in each initial cardiac image of one or more initial cardiac images of the one or more candidate cardiac motion phases further comprises:
   smoothing the each initial cardiac image of the one or more initial cardiac images using a low pass filter.

11. The method of claim 2, wherein the identifying a blood vessel centerline associated with the one or more images of the region of interest comprises:
- generating one or more images in a coronal plane and one or more images in a sagittal plane based on the one or more images of the region of interest;
- determining a blood vessel main body based on the one or more images in the coronal plane and the one or more images in the sagittal plane;
- filtering out one or more false positive vessels from the blood vessel main body; and
- identifying, based on the filtered blood vessel main body, a blood vessel center in each transverse layer associated with the one or more images of the region of interest.

12. The method of claim 2, wherein the obtaining the each cardiac image of the plurality of cardiac images by segmenting, based on a preset region including the blood vessel centerline, each image of the region of interest comprises:
- generating a transformed image of the region of interest by performing a top-hat transformation on the each image of the region of interest;
- generating an image including an intraventricular region by segmenting, based on a second threshold associated with gray levels of a soft tissue, the transformed image of the region of interest; and
- obtaining the each cardiac image of the plurality of cardiac images by segmenting, based on the preset region including the blood vessel centerline, the image including the intraventricular region.

13. The method of claim 1, wherein the determining a phase of interest for the cardiac cycle based on the plurality of quality indexes comprises:
- determining a maximum quality index in the plurality of quality indexes; and
- designating a phase of an image that has the maximum quality index as the phase of interest.

14. The method of claim 1, wherein the obtaining the target cardiac image of the phase of interest comprises:
- selecting the target cardiac image of the phase of interest from the plurality of cardiac images; or
- reconstructing the target cardiac image of the phase of interest based on a sub-set of projection data corresponding to the phase of interest.

15. The method of claim 1, wherein the determining a quality index for each cardiac image of a plurality of cardiac images comprises:
- determining, based on a maximum gray level of a plurality of elements of the each cardiac image, one or more thresholds for segmenting the each cardiac image;
- determining one or more sub-images of a region of interest by segmenting, based on the one or more thresholds, the each cardiac image; and
- determining, based on the one or more sub-images of the region of interest, a quality index for the each cardiac image.

16. The method of claim 1, wherein the plurality of cardiac images corresponding to the one or more cardiac motion phases are obtained by:
- obtaining the plurality of cardiac images corresponding to the one or more cardiac motion phases based on a plurality of sub-sets of projection data corresponding to the one or more cardiac motion phases.

17. A system for reconstructing a target cardiac image, comprising:
- at least one storage device storing a set of instructions; and
- at least one processor in communication with the storage device, wherein when executing the set of instructions, the at least one processor is configured to cause the system to perform operations including:
- determining a quality index for each cardiac image of a plurality of cardiac images corresponding to one or more cardiac motion phases of a cardiac cycle;
- determining a phase of interest for the cardiac cycle base on the plurality of quality indexes; and
- obtaining the target cardiac image of the phase of interest.

18. A non-transitory computer readable medium storing instructions, the instructions, when executed by at least one processor, causing the at least one processor to implement a method comprising:
- determining a quality index for each cardiac image of a plurality of cardiac images corresponding to one or more cardiac motion phases of a cardiac cycle;
- determining a phase of interest for the cardiac cycle base on the plurality of quality indexes; and
- obtaining the target cardiac image of the phase of interest.

19. The method of claim 1, wherein the quality index is determined based on a regularity degree of the cardiac image and/or a sharpness degree of the cardiac image.

20. The method of claim 1, wherein the determining a phase of interest for the cardiac cycle based on the plurality of quality indexes comprises:
- determining, among the one or more cardiac motion phases, a phase of interest based on the plurality of quality indexes.

* * * * *